US 8,727,968 B2

(12) United States Patent
Miyamoto et al.

(10) Patent No.: US 8,727,968 B2
(45) Date of Patent: May 20, 2014

(54) MEDICAL TREATMENT ENDOSCOPE WITH A POSITIONING MECHANISM

(75) Inventors: Manabu Miyamoto, Tokyo (JP); Yoshiaki Ito, Tokyo (JP); Hirokazu Tanaka, Tokyo (JP); Hideya Kitagawa, Tokyo (JP); Taro Iede, Tokyo (JP)

(73) Assignees: Olympus Corporation (JP); Olympus Medical Systems Corp. (JP)

( * ) Notice: Subject to any disclaimer, the term of this patent is extended or adjusted under 35 U.S.C. 154(b) by 818 days.

(21) Appl. No.: 12/552,392

(22) Filed: Sep. 2, 2009

(65) Prior Publication Data

US 2010/0081874 A1  Apr. 1, 2010

Related U.S. Application Data

(60) Provisional application No. 61/093,488, filed on Sep. 2, 2008.

(51) Int. Cl.
*A61B 1/00* (2006.01)
*A61B 1/04* (2006.01)
*A61B 17/04* (2006.01)
*A61B 17/08* (2006.01)

(52) U.S. Cl.
USPC ........... 600/106; 600/114; 600/104; 600/107; 606/147; 606/153

(58) Field of Classification Search
USPC ......... 600/106, 114, 137, 116, 102, 565, 115, 600/3, 113, 104, 129, 107; 606/85, 223, 606/147, 101, 40, 180, 115, 190, 46, 153; 128/852, 202.27
See application file for complete search history.

(56) References Cited

U.S. PATENT DOCUMENTS

| | | | | |
|---|---|---|---|---|
| 6,626,824 B2* | 9/2003 | Ruegg et al. | | 600/104 |
| 7,727,144 B2* | 6/2010 | Suzuki | | 600/106 |
| 7,942,868 B2* | 5/2011 | Cooper | | 606/1 |
| 7,967,813 B2* | 6/2011 | Cooper et al. | | 606/1 |
| 8,083,667 B2* | 12/2011 | Cooper et al. | | 600/104 |
| 8,088,062 B2* | 1/2012 | Zwolinski | | 600/106 |
| 8,353,815 B2* | 1/2013 | Okada | | 600/104 |

(Continued)

FOREIGN PATENT DOCUMENTS

| | | |
|---|---|---|
| JP | 03-295532 | 12/1991 |
| JP | 05-253-177 | 10/1993 |

(Continued)

OTHER PUBLICATIONS

International Search Report issued on Oct. 27, 2009 in connection with corresponding PCT application No. PCT/JP2009/065346.

(Continued)

*Primary Examiner* — John P Leubecker
*Assistant Examiner* — Ronald D Colque
(74) *Attorney, Agent, or Firm* — Ostrolenk Faber LLP

(57) ABSTRACT

Provided is a medical treatment endoscope including: an endoscope main body which includes an elongated insertion portion having a lumen and an image capturing mechanism disposed in a distal end of the insertion portion; an arm which is able to be inserted into or extracted from the lumen and has a treatment tool lumen for allowing an endoscope treatment tool to be inserted therethrough; and a positioning mechanism which positions a part of the arm inserted through the lumen with respect to the endoscope main body.

6 Claims, 36 Drawing Sheets

(56) References Cited

U.S. PATENT DOCUMENTS

| | | | |
|---|---|---|---|
| 2002/0198542 A1* | 12/2002 | Yamamoto et al. | 606/144 |
| 2003/0216749 A1* | 11/2003 | Ishikawa et al. | 606/108 |
| 2004/0138525 A1* | 7/2004 | Saadat et al. | 600/104 |
| 2004/0138529 A1* | 7/2004 | Wiltshire et al. | 600/144 |
| 2005/0065397 A1 | 3/2005 | Saadat et al. | |
| 2005/0203418 A1 | 9/2005 | Yamada et al. | |
| 2006/0184161 A1* | 8/2006 | Maahs et al. | 606/2 |
| 2006/0224041 A1* | 10/2006 | Okada | 600/106 |
| 2006/0258905 A1* | 11/2006 | Kaji et al. | 600/106 |
| 2007/0135803 A1* | 6/2007 | Belson | 606/1 |
| 2008/0051631 A1* | 2/2008 | Dejima et al. | 600/114 |
| 2008/0064921 A1* | 3/2008 | Larkin et al. | 600/104 |
| 2008/0065097 A1* | 3/2008 | Duval et al. | 606/130 |
| 2008/0065099 A1* | 3/2008 | Cooper et al. | 606/130 |
| 2008/0065102 A1* | 3/2008 | Cooper | 606/130 |
| 2008/0065105 A1* | 3/2008 | Larkin et al. | 606/130 |
| 2008/0065109 A1* | 3/2008 | Larkin | 606/130 |
| 2008/0065110 A1* | 3/2008 | Duval et al. | 606/130 |
| 2008/0071288 A1* | 3/2008 | Larkin et al. | 606/130 |
| 2008/0071289 A1* | 3/2008 | Cooper et al. | 606/130 |
| 2008/0171908 A1* | 7/2008 | Okada et al. | 600/114 |
| 2008/0183037 A1* | 7/2008 | Ichikawa et al. | 600/104 |
| 2008/0200756 A1* | 8/2008 | Okada et al. | 600/106 |
| 2008/0255424 A1* | 10/2008 | Durgin et al. | 600/156 |
| 2008/0269558 A1* | 10/2008 | Yahagi et al. | 600/106 |
| 2008/0287737 A1 | 11/2008 | Dejima | |
| 2008/0287963 A1* | 11/2008 | Rogers et al. | 606/130 |
| 2009/0024141 A1* | 1/2009 | Stahler et al. | 606/130 |
| 2010/0125285 A1* | 5/2010 | Sewell et al. | 606/130 |
| 2011/0015483 A1* | 1/2011 | Barbagli et al. | 600/108 |
| 2011/0015484 A1* | 1/2011 | Alvarez et al. | 600/109 |
| 2011/0015648 A1* | 1/2011 | Alvarez et al. | 606/130 |

FOREIGN PATENT DOCUMENTS

| | | | |
|---|---|---|---|
| JP | 08-168492 | | 7/1996 |
| JP | 08-510676 | | 11/1996 |
| JP | 2005-253615 | | 9/2005 |
| JP | 2006-314714 | | 11/2006 |
| JP | 2007-511247 | | 5/2007 |
| JP | 2007-151595 | * | 6/2007 |
| JP | 2008-012044 | | 1/2008 |
| JP | 2008-017859 | | 1/2008 |
| JP | 2008-173472 | | 7/2008 |
| JP | 2008-194302 | | 8/2008 |
| WO | WO 94/28784 | | 12/1994 |
| WO | WO 2008/051951 | | 5/2008 |

OTHER PUBLICATIONS

Office Action issued by the Japanese Patent Office on Aug. 7, 2012 in connection with corresponding Japanese Patent Application No. 2009-137986.

Translation of Office Action issued by the Japanese Patent Office on Aug. 7, 2012 in connection with corresponding Japanese Patent Application No. 2009-137986.

Office Action issued by the Japanese Patent Office on Jan. 8, 2013 in connection with corresponding Japanese Patent Application No. 2009-137986.

Translation of Office Action issued by the Japanese Patent Office on Jan. 8, 2013 in connection with corresponding Japanese Patent Application No. 2009-137986.

Office Action mailed by Japanese Patent Office on May 14, 2013 in connection with corresponding Japanese Patent Application No. 2009-137986 with English translation.

* cited by examiner

MEDICAL TREATMENT ENDOSCOPE WITH A POSITIONING MECHANISM

BACKGROUND OF THE INVENTION

1. Field of the Invention

The present invention relates to a medical treatment endoscope.

2. Description of Related Art

Laparoscopic procedures are a conventionally known technique which may be employed in place of making a large incision in the abdominal wall when performing a medical procedure such as observing or treating an organ in the human body. In such laparoscopic procedures, a plurality of openings are made in the abdominal wall and procedures are performed by inserting a laparoscope and forceps or other such instruments into these openings. Laparoscopic procedures provide the benefit of lessening the burden placed on the patient because only small openings need to be made in the abdominal wall.

In recent years, methods of performing procedures by inserting a flexible endoscope via the mouth, nose, anus, or other natural orifice of the patient have been proposed as methods which further reduce the burden on the patient. An example of a medical treatment endoscope used in such procedures is disclosed in U.S. Patent Application Publication No. 2005/0065397.

In the medical treatment endoscope disclosed in this reference, arm members that have a bendable distal end are respectively inserted into a plurality of lumens disposed within a flexible insertion portion that is inserted into the body via the mouth of the patient. By inserting respective instruments through these arm members, the procedure site can be approached from different directions with the various instruments. Accordingly, a plurality of procedures can be carried out in continuum by means of a single endoscope inserted into the body.

DETAILED DESCRIPTION OF THE INVENTION

The medical treatment endoscope according to the first embodiment of the present invention will now be explained with reference to FIGS. 1 through 11.

Figure 1:
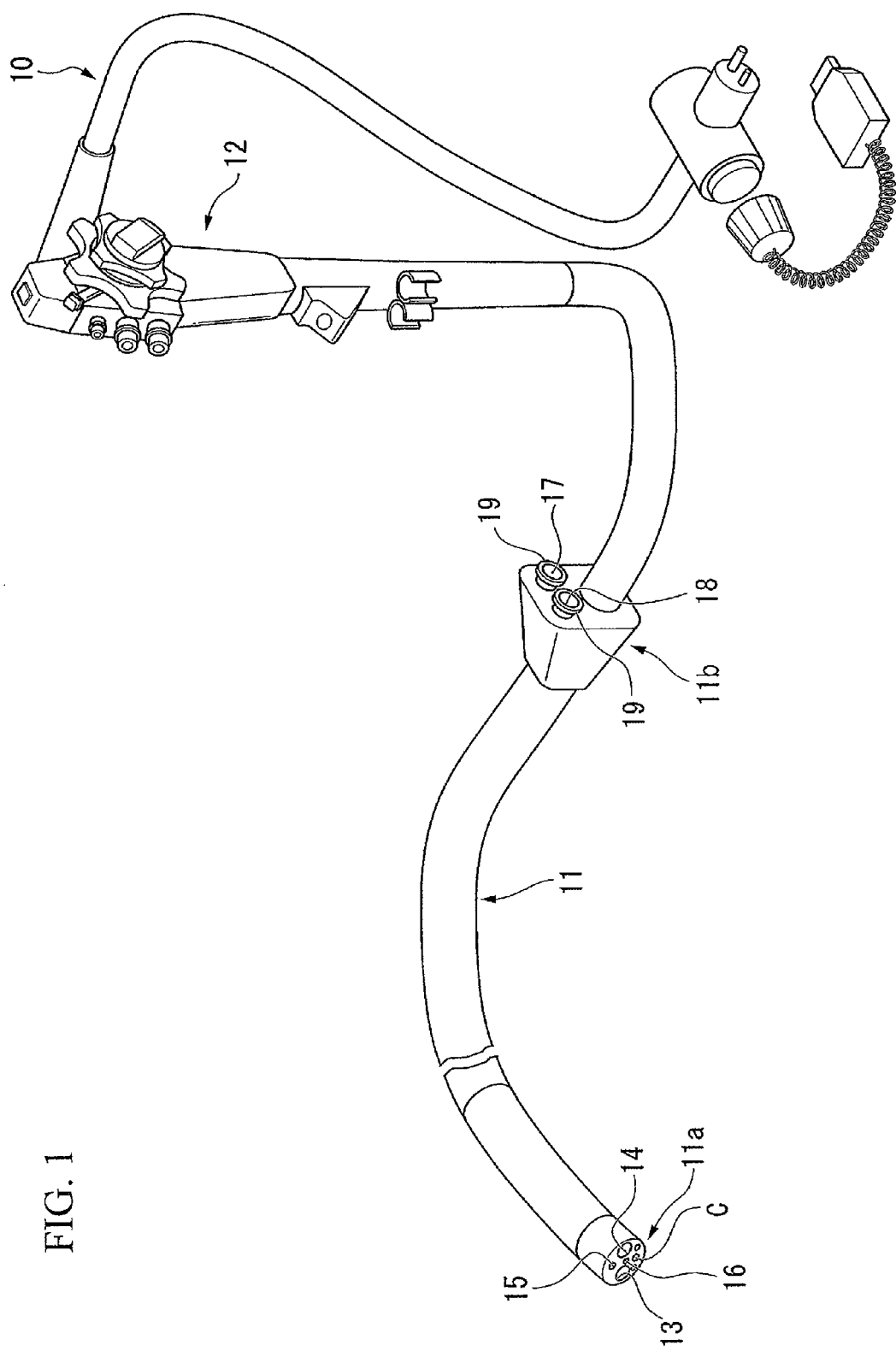
FIG. 1 is a view showing the medical treatment endoscope according to a first embodiment of the present invention.
Figure 2:
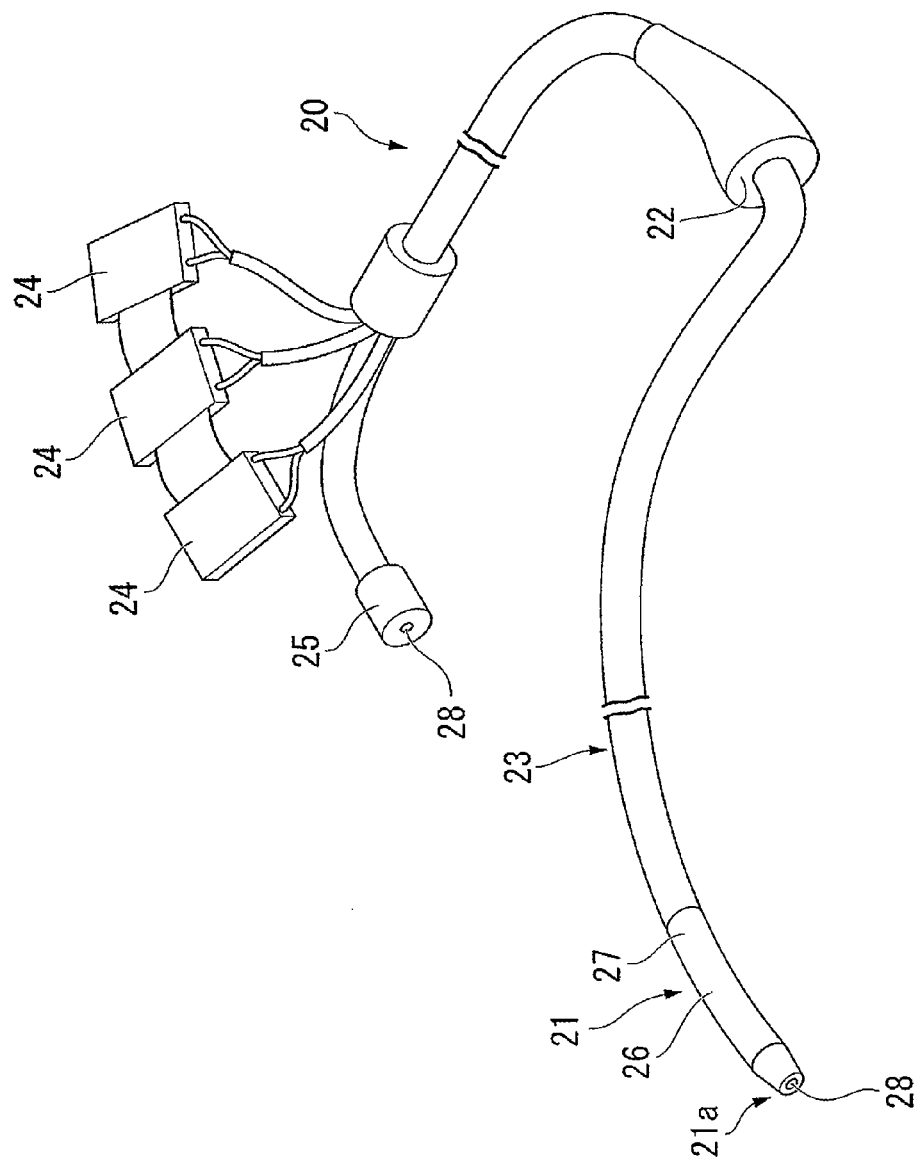
FIG. 2 is a view showing the arm of the medical treatment endoscope.

As shown in FIG. 1, the medical treatment endoscope according to this embodiment is composed of the provision of a medical treatment endoscope main body 10 and the arm 20 shown in FIG. 2. The medical treatment endoscope main body 10 and the arm 20 are combined to function as a medical treatment endoscope 1 (see FIG. 4).

The medical treatment endoscope main body 10 is provided with an insertion portion 11 on the distal end side thereof which is inserted into the body cavity of the patient, and an operating portion 12 which is connected to the proximal end side of the insertion portion 11. The insertion portion 11 is in the form of a flexible long tube. Two large diameter lumens 13, 14, which have relatively large diameters, and small diameter lumens 15,16, which have relatively small diameters, are provided within the insertion portion 11. The small diameter lumens 15,16 extend toward the operating portion 12 side. The small diameter lumen 15 is used as an instrument channel into which an endoscopic instrument or the like may be inserted. The small diameter lumen 15 can also be employed as a suction pathway. The small diameter lumen 16 is employed for sending air or water into the distal end 11a of the insertion portion 11. The large diameter lumens 13,14 extend from the distal end 11a of the insertion portion 11 to the middle part 11b. Middle openings 17,18, which open on the outer peripheral surface of the insertion portion 11, are present at the middle part 11b. Stoppers 19 are provided to the middle openings 17,18 and are formed so that the outer periphery of the end portion thereof expands in the radial direction. In addition, while not an essential component of the present invention, the inner walls of the large diameter lumens 13,14 are reinforced by a braid tube in which there is braided metal wire. In addition, an image capturing mechanism C is provided to the distal end 11a of the medical treatment endoscope main body 10.

As shown in FIG. 2, the medical treatment endoscope 1 is further provided with an arm 20 which has a cylindrical portion, the diameter of which is roughly equal to the inner diameter of the large diameter lumens 13,14. The arm 20 is formed so that it can be freely inserted and withdrawn with respect to the large diameter lumens 13,14 of the medical treatment endoscope. The arm 20 is formed through the provision of an arm distal end part 21 which bends with respect to the axis thereof; a long tubular arm middle part 23 which has a groove 22 that engages with a stopper 19; cartridges 24 which are provided with an operator mechanism, not shown in the figures, for bending the arm distal end part 21; and a connector 25 which is formed to the proximal end side of the arm 20. The arm distal end part 21 is provided with a first bending part 26 which is located at the middle part of the arm distal end part 21 and bends the arm distal end part 21 in a specific direction; and a second bending part 27 which is located at the bottom portion when the arm distal end part 21 is projected out from the distal end 11a of the medical treatment endoscope main body 10, and which is positioned farther toward the proximal end side than the first bending part 26. An arm member such as disclosed in U.S. patent application Ser. No. 12/024,704 (MEDICAL TREATMENT ENDOSCOPE) may be cited as an example of the design for a bending part such as this. The first bending part 26 and the second bending part 27 are connected to the cartridges 24 via wires, not shown in the figures, which are provided to first the bending part 26 and the second bending part 27 respectively, and are designed to undergo bending manipulation from the proximal end side of the arm 20.

An instrument lumen 28 is formed inside the arm 20 for inserting an instrument for endoscopic use from the proximal end toward the distal end. The instrument lumen 28 communicates with an instrument lumen 33 which is provided to the arm operating portion 30. A tapered portion 21a is formed to the distal end of the arm 20, the diameter of this tapered portion 21 gradually decreasing approaching the distal end. The connector 25 can be connected to a connector 31 which is provided to the arm operating portion 30 shown in FIG. 3. In addition, the cartridges 24 to which wires are connected are fixed in place to one of the receiving parts 32 provided in the arm operating portion 30.

Figure 3:
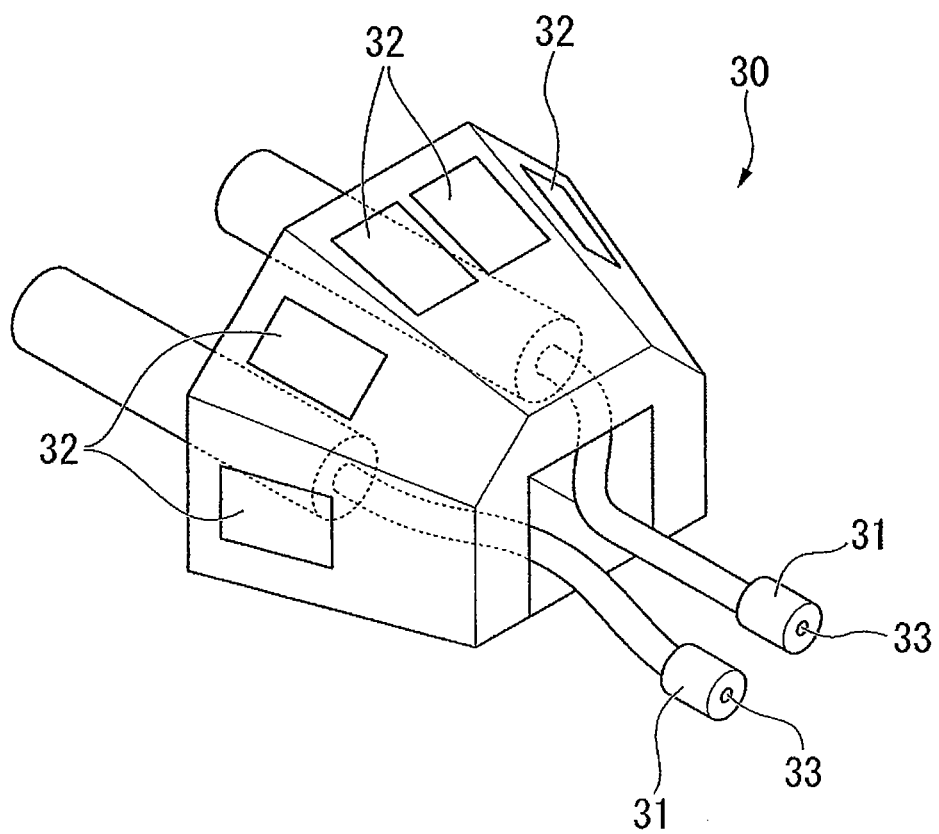
FIG. 3 is a view showing an example of the arm operating portion employed in the medical treatment endoscope.

As shown in FIG. 3, an arm operating portion of a suitable design having a connector 31 which can connect to the connector 25 of the arm 20, and a receiving part 32 which can connect to the cartridge 24 may be employed for the arm operating portion 30. An example of such an arm operating portion is disclosed in U.S. patent application Ser. No. 12/024,704, MEDICAL TREATMENT ENDOSCOPE.

The action of the above-designed medical treatment endoscope during use will now be explained with reference to FIGS. 1 to 3.

The medical treatment endoscope 1 is prepared with the medical treatment endoscope main body 10 and the arm 20 in a separated state. The medical treatment endoscope main body 10 is sterilized. The arm 20 is also sterilized in a similar manner.

The connector 25 on the proximal end side of the arm 20 is connected to the connector 31 on the distal end side of the arm operating portion 30. The cartridges 24 on the proximal end side of the arm 20 are fixed in place to the receiving parts 32 of the arm operating portion 30.

Next, the operator (user) inserts the medical treatment endoscope main body 10 via a natural orifice, such as the mouth, etc., of the patient from the distal end 11a, and guides the device so as to position the distal end 11a near the target area where the procedure is to be performed. At this time, after inserting the distal end 11a into the stomach, etc., it is possible to guide the distal end 11a into the vicinity of the target area where the procedure is to be performed, by incising the stomach wall, etc. using an endoscopic instrument, and advancing the distal end 11a into a body cavity such as the abdominal cavity via the stomach.

Figure 4:
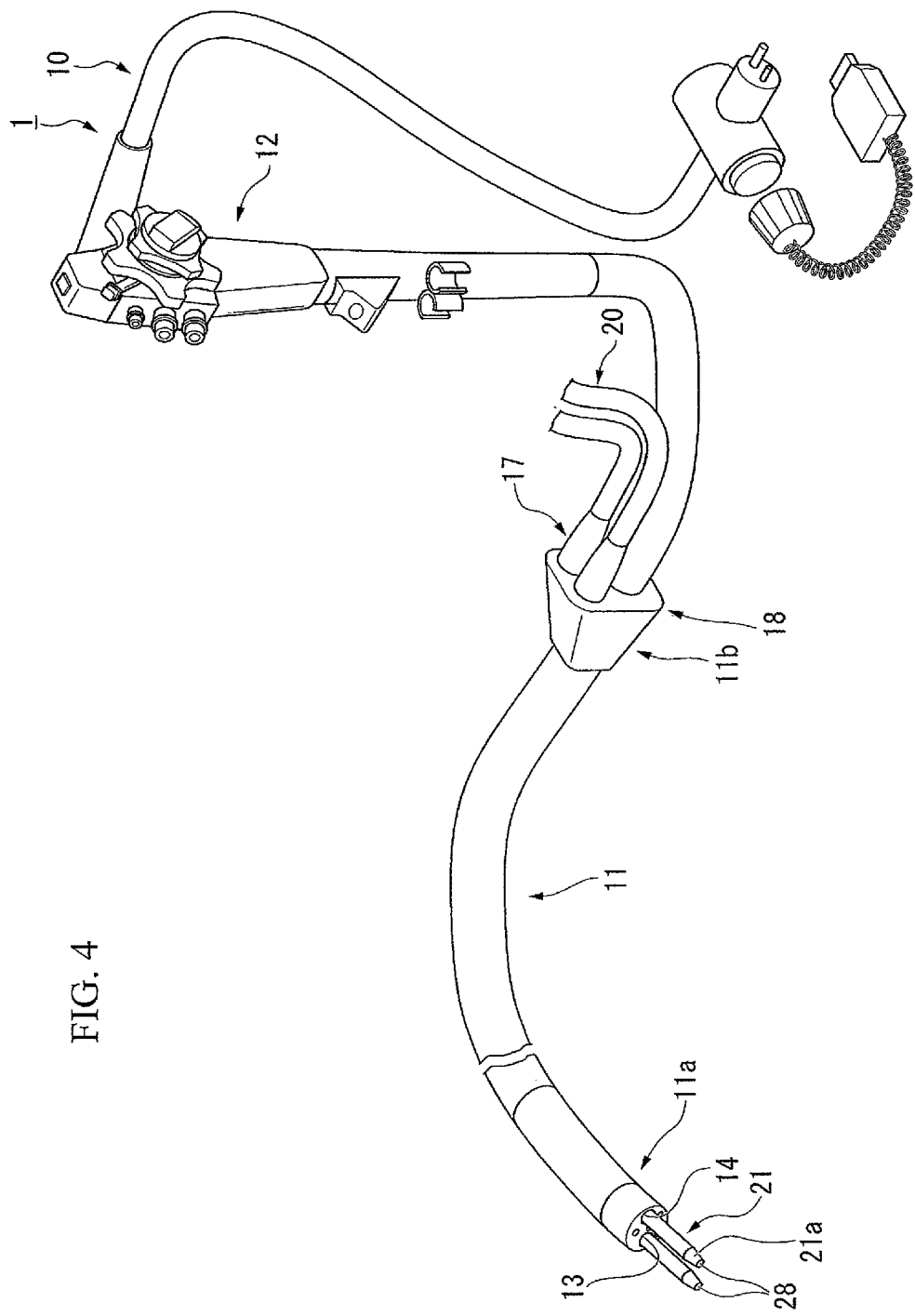
FIG. 4 is a view showing the action during use of the medical treatment endoscope.

As shown in FIG. 4, the arm distal end part 21 is inserted from the middle openings 17,18 into the large diameter lumens 13,14 as the distal end 11a of the medical treatment endoscope main body 10 is supported so that it does not move. The arm distal end part 21 is then projected out from the distal end 11a of the medical treatment endoscope main body 10. When the arm distal end part 21 is projected out from the distal end 11a of the medical treatment endoscope main body 10, the stoppers 19 formed to the middle openings 17,18 are caught in the groove 22 that is formed in the middle part of the arm 20. The relative positions of the arm 20 and the medical treatment endoscope main body 10 in the axial direction are fixed in place at the middle openings 17,18.

Figure 5:
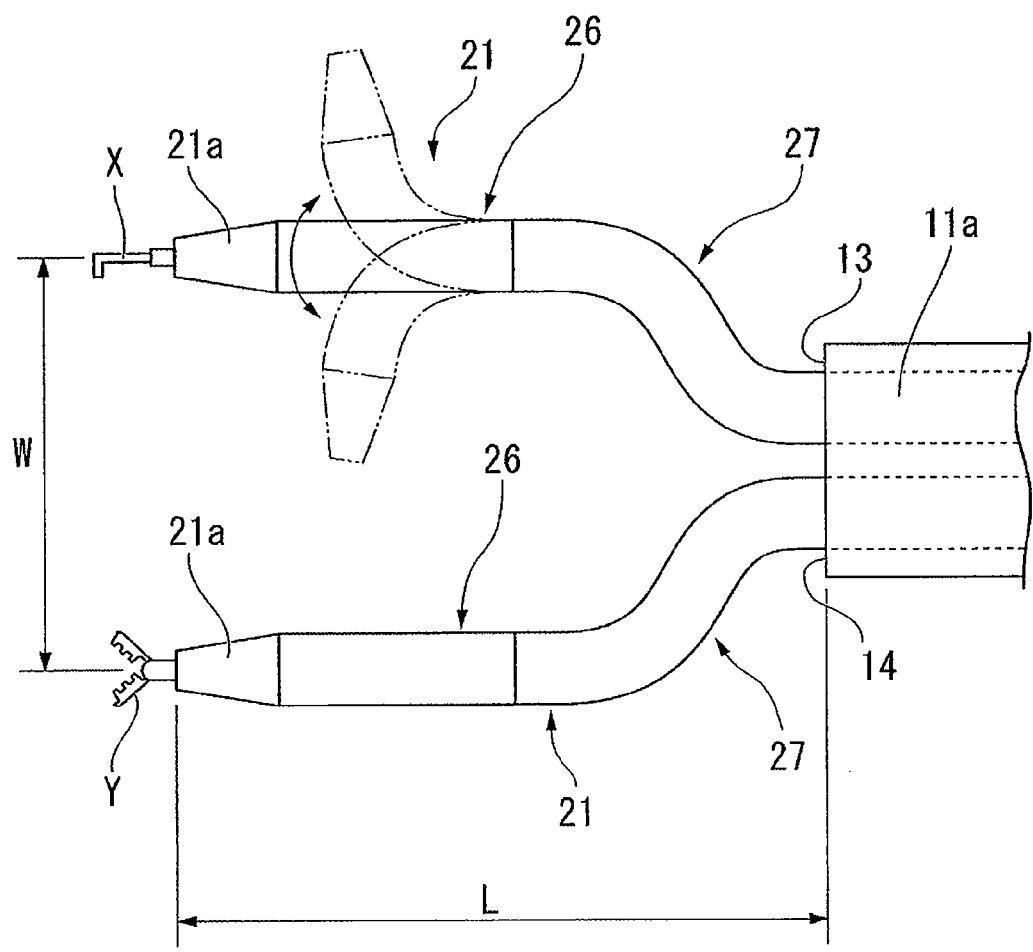
FIG. 5 is a view showing the action during use of the medical treatment endoscope.

As shown in FIG. 5, once the arm 20 has been inserted into the large diameter lumens 13,14, the operator inserts an endoscopic instrument, such as a high-frequency knife X or gripping forceps Y, from the hand held side at arm operating portion 30, via the instrument lumen 33, into the instrument lumen 28 of the arm 20, and projects the instrument out from the tapered portion 21a of the arm 20. The operator manipulates the cartridges 24 for operating the second bending part at the arm operating portion 30, and applies traction on a wire, not shown in the figures, which is connected to the second bending part 27, pulling the wire toward the proximal end side. The second bending part 27 is connected to the wire bends as a result. The first bending part 26 moves radially away from the central axis of the medical treatment endoscope main body 10. With this arrangement in place, the operator operates the cartridges 24 for operating the first bending part 26, and bends the first bending part 26. The tapered parts 21a of the arm 20 can be manipulated so as to be positioned at the target site. The operator carries out the appropriate procedure on the target site while relying on the image shown on a monitor, not shown in the figures, displayed by the image capturing mechanism C provided to the distal end 11a of the medical treatment endoscope main body 10.

Once the treatment is completed, the operator operates the cartridges 24 to release the bending of the first bending part 26 and the second bending part 27 of the arm 20. Next, traction toward the proximal end side is applied on the arm 20 to release the engagement between stoppers 19 and the groove 22. The arm 20 is then withdrawn from the large diameter lumens 13,14. Note that the operator may withdraw the endoscopic instrument inserted into the medical treatment lumen 28 prior to withdrawing the arm 20. The medical treatment endoscope main body 10 is withdrawn from the body cavity, concluding the continuous procedure. Note that the withdrawal of the arm 20 may be carried out after withdrawing the medical treatment endoscope main body 10 from the body cavity.

In a conventional medical treatment endoscope, the arm distal end is fixed in place to the medical treatment endoscope. Accordingly, this is problematic because, when inserting the medical treatment endoscope into a body cavity with the arm distal portion in the attached state, it is necessary to insert the medical treatment endoscope into the body cavity very carefully so that the arm distal end, which functions as a projection relative to the medical treatment endoscope, does not contact the inside of the body cavity. Moreover, this is also problematic because the forward visual field is poor due to interference by the arm. In addition, since the arm distal end is fixed in place to the medical treatment endoscope, the arm can become a hindrance when carrying out other procedures which do not require the arm when the medical treatment endoscope is inserted into the body cavity. In this case, the operator may withdraw the medical treatment endoscope from the body cavity and insert another endoscope into the body cavity. However, time and effort are required to exchange the medical treatment endoscopes from the body cavity, so that the treatment becomes problematically complicated.

In a medical treatment endoscope 1 having a design such as the present embodiment, the arm 20 can be employed by insertion in a freely inserting and retracting manner with respect to the medical treatment endoscope main body 10 via the large diameter lumens 13,14. Since the medical treatment endoscope main body 10 can be inserted into the body cavity without attaching the arm 20, there is no extraneous projecting object during insertion, thus facilitating the insertion of the medical treatment endoscope 1.

In the medical treatment endoscope 1, it is possible to withdraw the arm 20 itself from the medical treatment endoscope main body 10 without withdrawing the medical treatment endoscope 1 from the body cavity. As a result, it is possible to remove or exchange the arm distal end part 21. By decreasing the removal and insertion of the medical treatment endoscope main body 10 with respect to the body cavity during a procedure, the trouble and time required by the procedure can be decreased. In addition, it is also possible to employ large diameter suturing devices, ultrasonic instruments, high frequency cutting and coagulating instruments and the like in place of the arm 20.

Next, a second embodiment of the present invention will be explained with reference to FIG. 6. The medical treatment endoscope 40 of this embodiment differs from the medical treatment endoscope 1 described above in that there is provided an elongated tube which is connected to the middle opening and extends to the operator.

Note that structural elements that are equivalent to the preceding first embodiment will be assigned the same numeric symbol and a redundant explanation thereof will be omitted.

Figure 6:
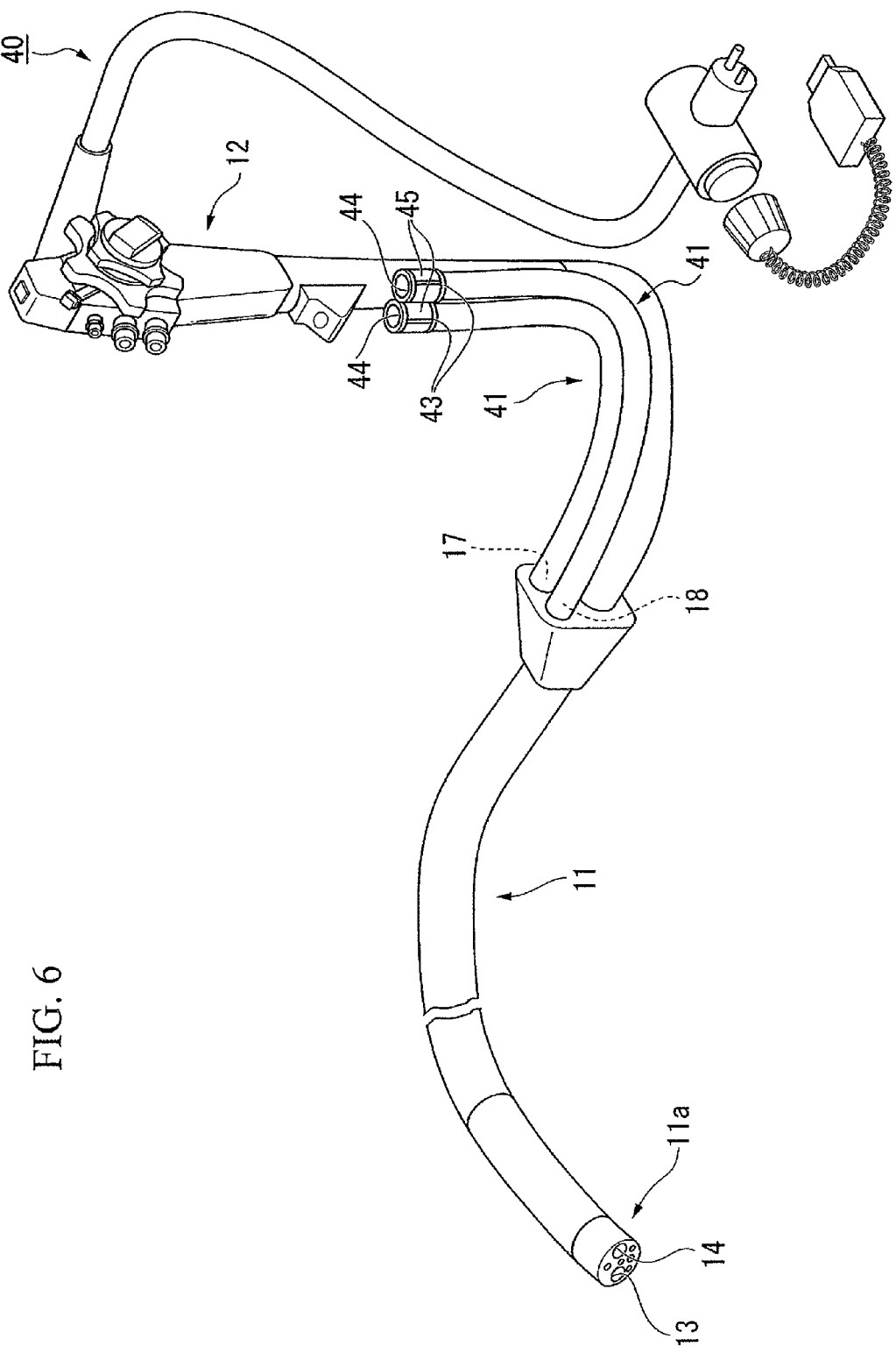
FIG. 6 is a view showing the medical treatment endoscope according to a second embodiment of the present invention.

As shown in FIG. 6, in the medical treatment endoscope 40 of this embodiment, elongated tubes 41 are attached in place of the arm 20 to each of the middle openings 17,18, and extend the middle openings 17,18 toward the operating portion 12 side. The elongated tube 41 is a tubular member that has a groove 42, not shown in the figures, on the distal end side that engages in the stopper 19, and has an inner diameter that is equal to the inner diameter of the large diameter lumens 13,14. A connector 43 is provided to the proximal end side of the elongated tubes 41. The connector 43 has an opening 44 that has the same size and shape as the large diameter lumens 13,14 in radial cross-section. The connector 43 can be fixed in place by engaging with the holder 45 that is formed to the operating portion 12 of the medical treatment endoscope main body 10.

In the medical treatment endoscope 40 according to this embodiment, by attaching the elongated tube 41 to one or both of the two large diameter lumens 13,14, it is possible to use the device by directly inserting an endoscopic instrument from the mouth ring on the operator side into the large diameter lumens. In this type of medical treatment endoscope, the opening 44, which functions as the opening for the large diameter lumens 13,14, is positioned at a site near the operating portion 12. Thus, it becomes easy for the operator who is supporting the medical treatment endoscope and carrying out the procedure to manipulate an endoscopic instrument via the large diameter lumen. Further, a design may be provided in which the elongated tube is connected to only the middle opening of one of the two large diameter lumens 13,14, and the arm is connected to the middle opening of the other large diameter lumen. Thus, it becomes easy to carry out cooperative operations wherein one operator performs manipulation of the arm at the arm operating portion and another operator performs manipulations of the endoscopic instrument at the operator.

Next, a third embodiment of the present invention will be explained with reference to FIGS. 7 and 8. The medical treatment endoscope according to this embodiment differs from the preceding medical treatment endoscope 1 in that the large diameter lumen branches toward the operating portion side in the area of the middle opening, and the end of the large diameter lumen is open on the operating portion side.

Figure 7:
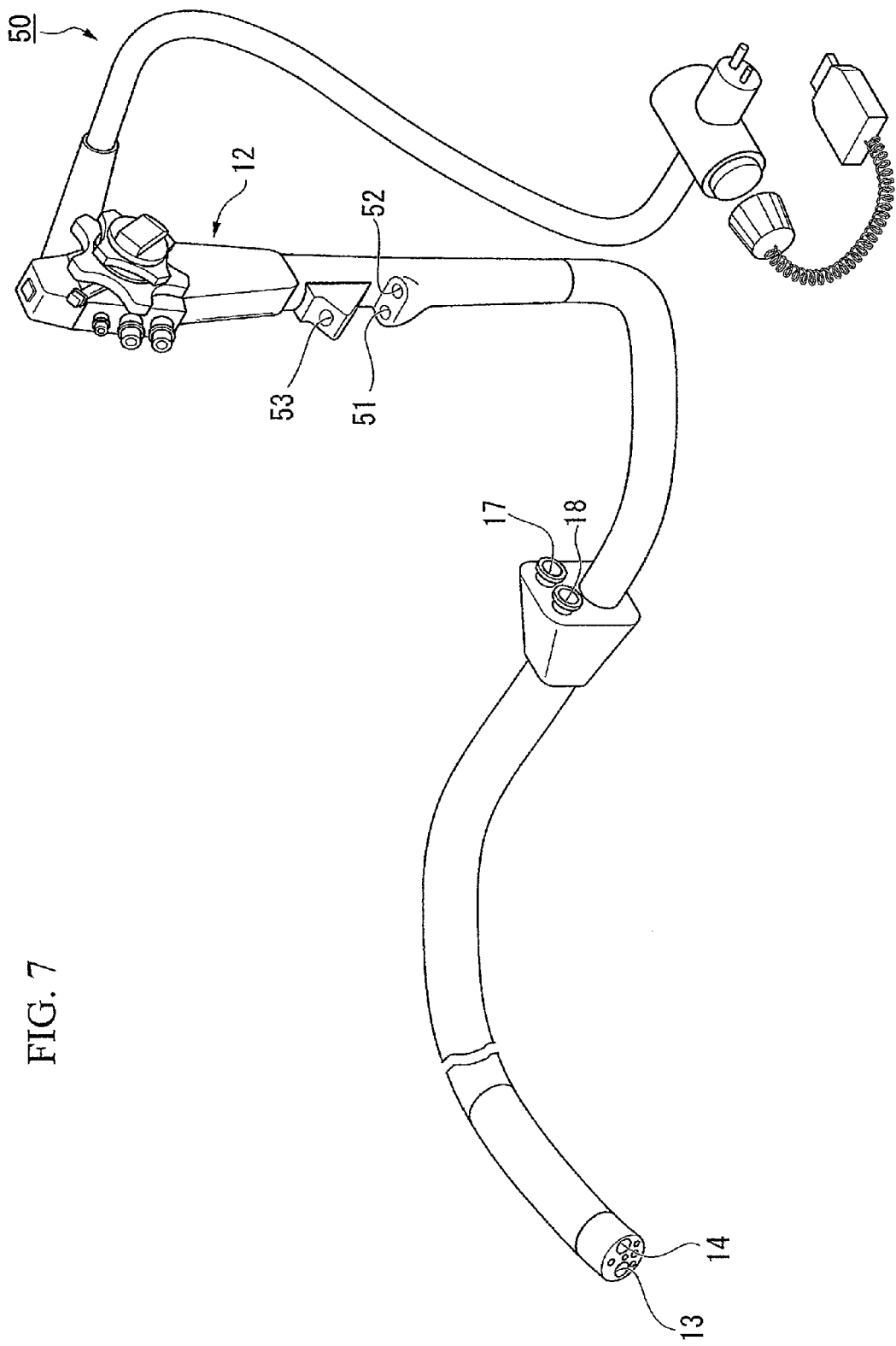
FIG. 7 is a view showing the medical treatment endoscope according to a third embodiment of the present invention.
Figure 8:
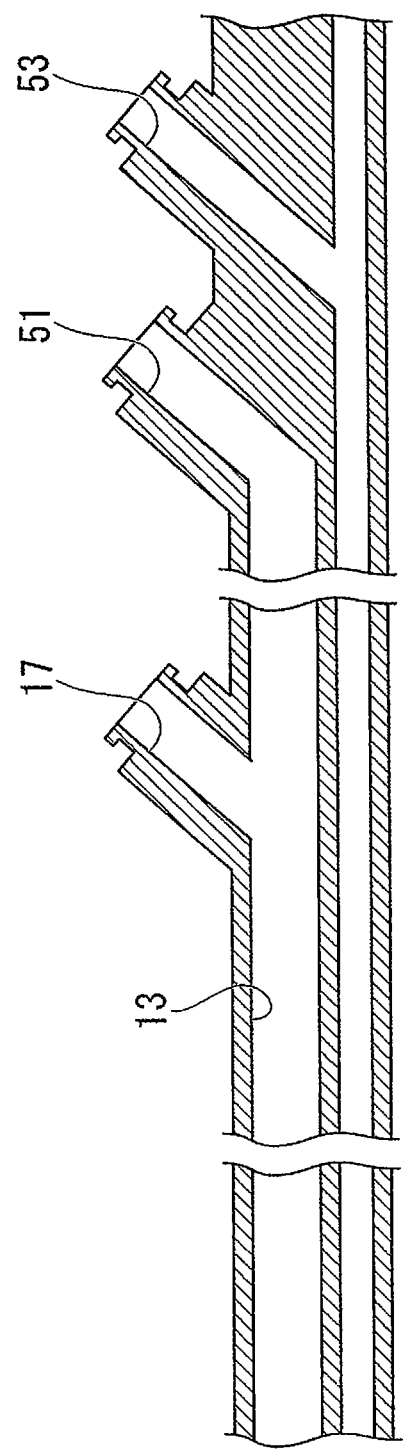
FIG. 8 is a cross-sectional view showing the medical treatment endoscope.

As shown in FIGS. 7 and 8, in the medical treatment endoscope 50 according to this embodiment, the large diameter lumens 13,14 extend from the area of the middle openings 17,18 and branch toward the operating portion 12 side. The large diameter lumens 13,14 have proximal end openings 51,52 which are open to the outside at the operating portion 12. Airtight valves, not shown in the figures, for restricting communication with the outside are provided respectively to the middle openings 17,18 and the proximal end openings 51,52.

In this embodiment, when employing an endoscopic instrument that that is wider than the typical endoscopic instrument, such that it will not enter the instrument lumen 53 which is provided to the operating portion 12, it is possible to guide the endoscopic instrument to the distal end of the endoscope from the proximal end openings 51,52 provided to the operating portion 12 via the large diameter lumens 13,14. The device can also be employed with a plurality of endoscopic instruments inserted into the inner space of one large diameter lumen.

By providing proximal end openings 51,52 near the operating portion 12, it is not necessary to attach or release an elongated tube 41, etc. such as provided to the medical treatment endoscope 40 according to the second embodiment.

Next, a fourth embodiment of the present invention will be explained with reference to FIG. 9. The medical treatment endoscope of this embodiment differs from the preceding medical treatment endoscopes in that the above-described proximal end opening is present and a tube is provided to the middle openings and extends the large diameter lumen toward the arm operating portion side.

Figure 9:
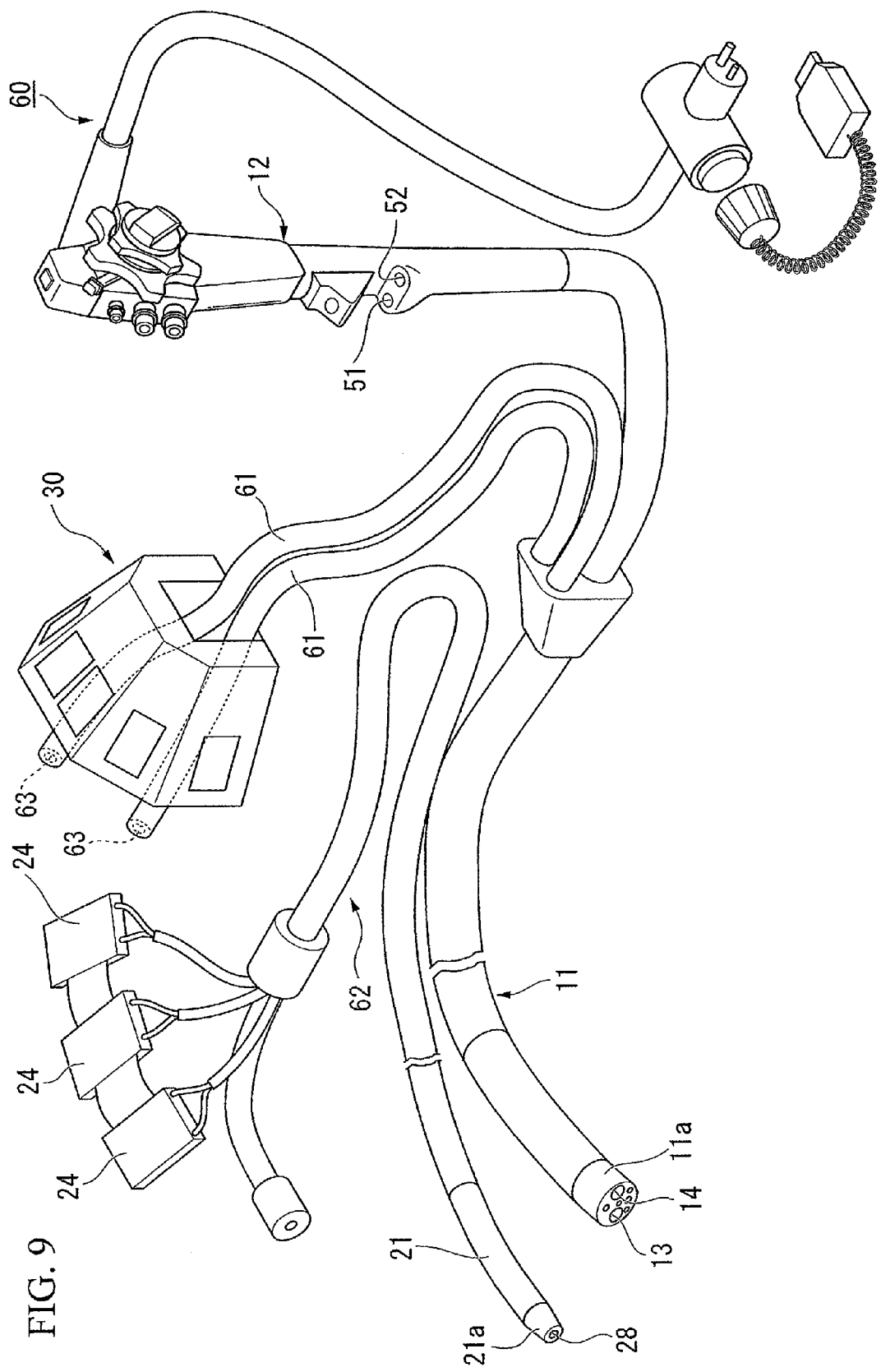
FIG. 9 is a view showing the medical treatment endoscope according to a fourth embodiment of the present invention.

As shown in FIG. 9, the medical treatment endoscope 60 according to this embodiment is provided with tubes 61 that continue from the arm operating portion 30 to the middle openings 17,18. In addition, an arm 62 is provided in place of the arm 20 in this embodiment, arm 62 having a distal end that is tapered in the same manner as arm 20, and an outer diameter that permits free advance and retraction with respect to the large diameter lumens 13,14 at far as the proximal end side. The tubes 61 are cylindrical in shape, having an inner diameter of the same size as the inner diameter of the large diameter lumens 13,14. In this embodiment, a design is provided in which the arm distal end part 21 of the arm 62 is inserted from the proximal end opening 63 of the tube 61 and is projected out from the distal end 11a of the medical treatment endoscope 60.

By providing this design, the insertion and release of the arm 62 is enabled in the vicinity of the arm operating portion 30. Thus, the operator responsible for operation of the arm 62 can carry out the insertion and release of the arm 62 from the location of the arm operating portion 30. Moreover, since a design is provided with enables the operator to manipulate endoscopic instruments other than the arm 62, it is possible for a single person to manipulate both the arm 62 and an endoscopic instrument without moving away from the arm operating portion 30.

Next, a fifth embodiment of the present invention will be explained with reference to FIGS. 10 through 12. The medical treatment endoscope 70 according to this embodiment differs from the preceding medical treatment endoscopes in the design of the distal end of the medical treatment endoscope main body.

Figure 10:
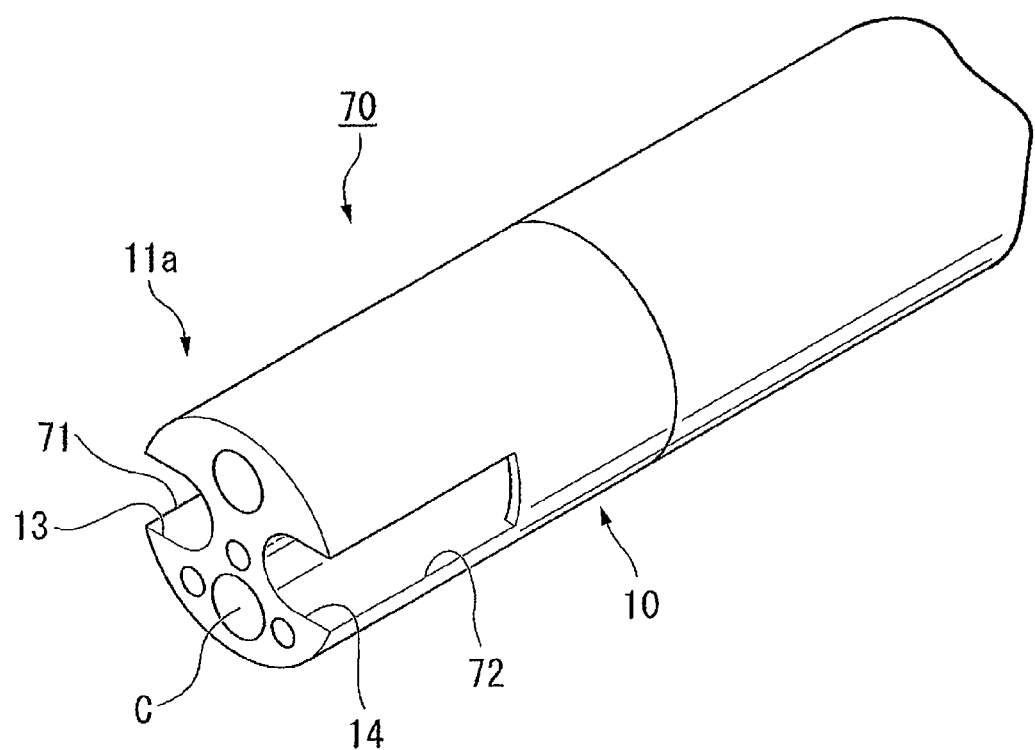
FIG. 10 is an enlarged view showing the distal end of the medical treatment endoscope according to a fifth embodiment of the present invention.
Figure 11:
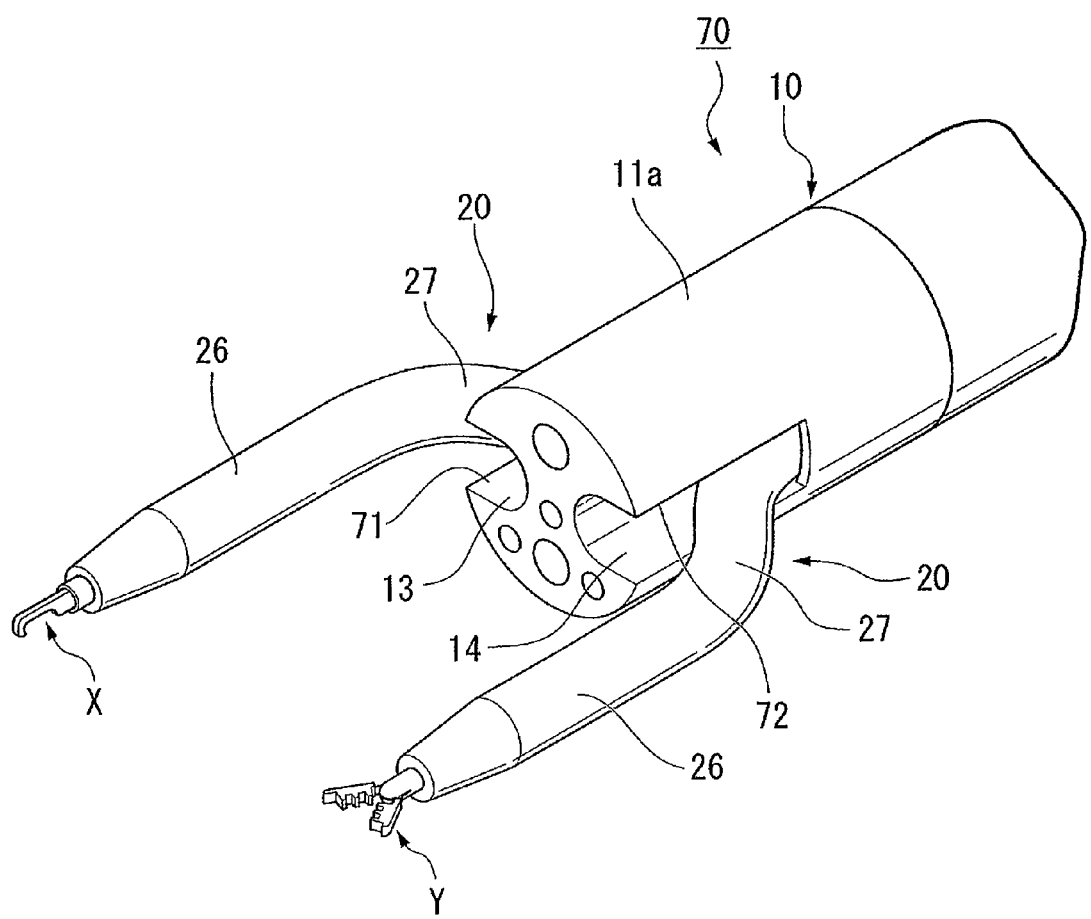
FIG. 11 is an enlarged view showing the distal end of the medical treatment endoscope during.

As shown in FIG. 10, in this medical treatment endoscope 70, the openings of the two large diameter lumens 13,14 and an image capturing mechanism C for capturing images inside the body are disposed to the distal end 11a of the medical treatment endoscope main body 10. The openings of the large diameter lumens have lateral openings 71,72 which continue from the distal end along the outer peripheral surface so that a portion of the outer peripheral surface is cut out. The positional relationship when attaching the arm 20 to the large diameter lumens 13,14 is such that the proximal end of the second bending part 27 is farther toward the proximal end side than the distal end of the medical treatment endoscope main body 10 of the medical treatment endoscope 70, as shown in FIG. 11.

Figure 12:
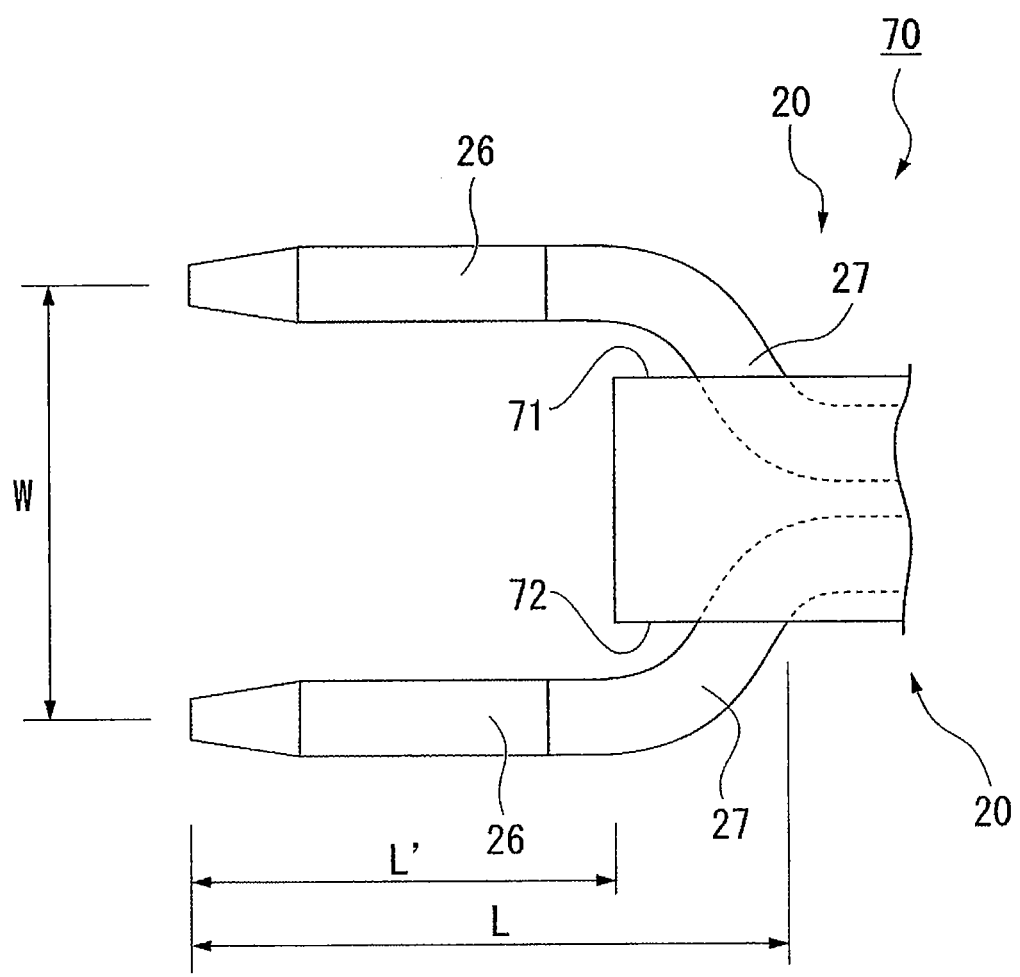
FIG. 12 is an enlarged view showing the distal end of the medical treatment endoscope during use.

In a medical treatment endoscope of this design, the distance L' from the distal end of the arm 20 to the distal end of the medical treatment endoscope 70 is shorter than the distance L from the distal end of the arm 20 to the proximal end of the second bending part 27, as shown on FIG. 12. An image capturing mechanism C is disposed to the distal end of the medical treatment endoscope 70. Since it is possible to shorten the distance from the distal end of the arm 20 to the image capturing mechanism C in this type of design, it is possible to capturing images in the vicinity of the endoscopic instrument, etc., which is inserted into the arm 20 in greater detail. Accordingly, the operator can more easily carry out a procedure using endoscopic instruments by using the medical treatment endoscope 70.

Next, a sixth embodiment of the present invention will be explained with reference to FIGS. 13 and 14. The medical treatment endoscope according to this embodiment differs from the preceding medical treatment endoscopes with respect to the internal structure of the arm distal end.

Figure 13:
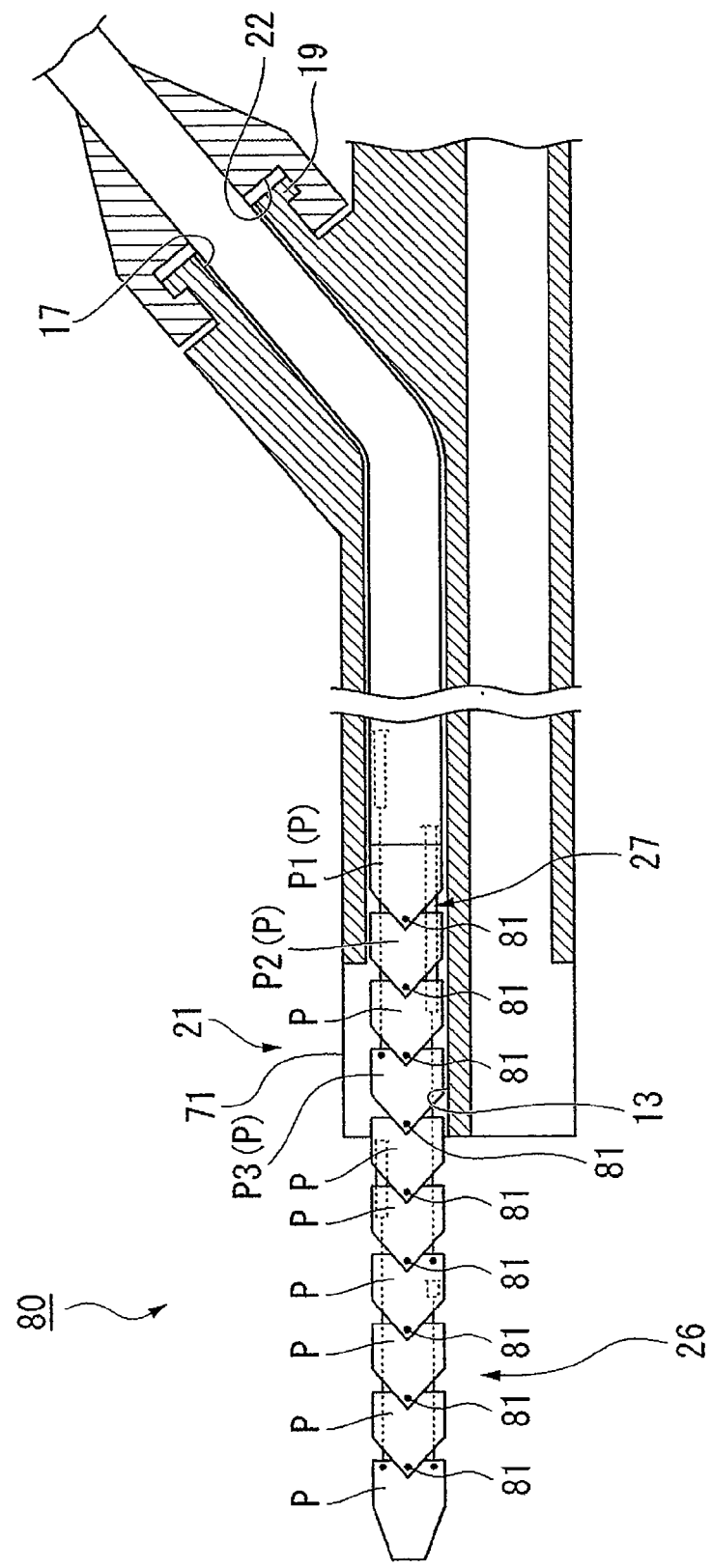
FIG. 13 is a view in partial cross-section of the action during use of the medical treatment endoscope according to a sixth embodiment of the present invention.
Figure 14:
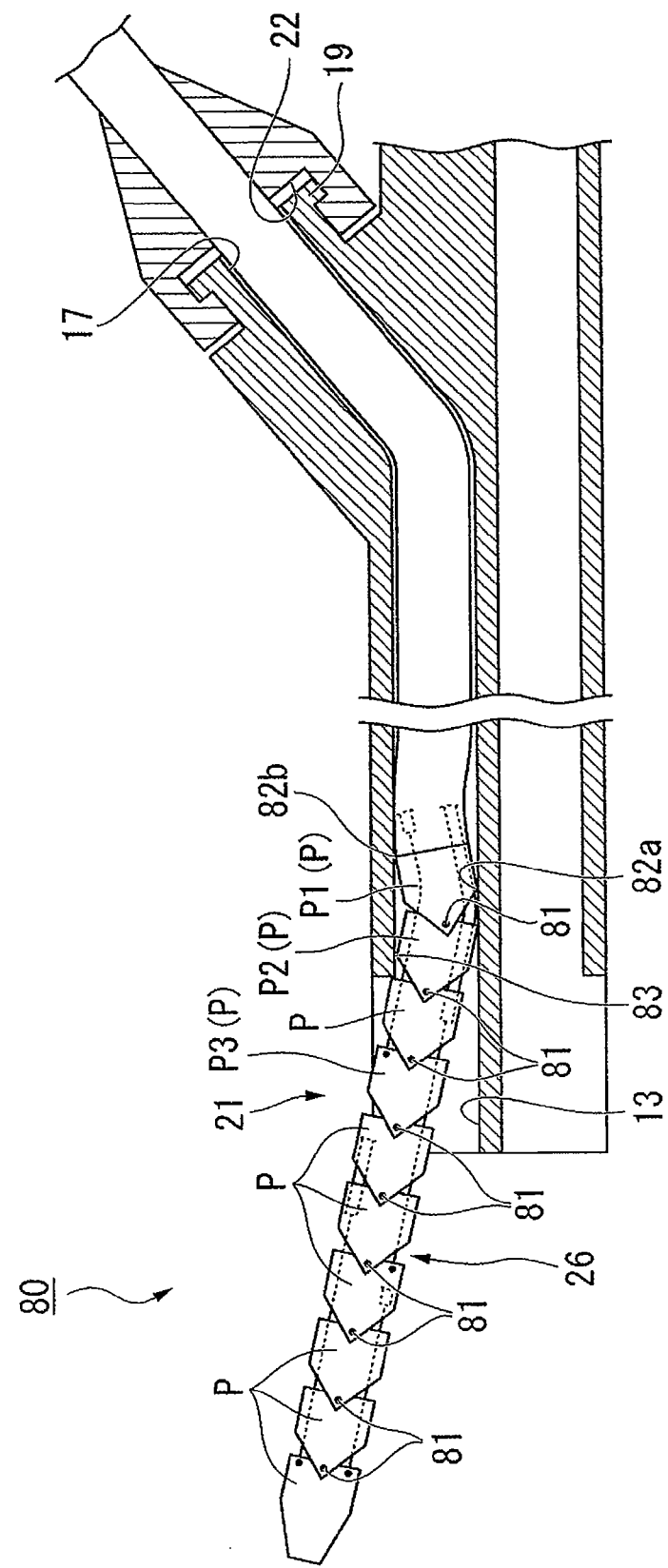
FIG. 14 is a view in partial cross-section of the action during use of the medical treatment endoscope.

As shown in FIG. 13, in the medical treatment endoscope 80 according to this embodiment, the arm distal end part 21 has a plurality of cylindrical members P that are connected along the axial direction. The plurality of cylindrical members P have connections 81 at opposite positions on the wall thereof. The respective multiple cylindrical members P are connected in a freely swinging manner centered on the axis that links the connections 81. Further, while omitted from the FIGS. 13 and 14, the arm distal end 21 is covered with a covering member. A braid tube or resin tube such as described above may be employed for this covering member. Note, however, that a structure which is not covered with a braid tube or a covering member may be employed for the arm distal end part 21. When the arm 20 is attached to the medical treatment endoscope main body, the second bending part 27 is positioned farther toward the proximal end side than the lateral opening 71. In this case, the first cylinder P1, which is farthest toward the proximal end side from among the proximal end cylindrical members, and the second cylinder P2 connected to the first cylinder P1, are positioned inside the large diameter lumen 13 (or the large diameter lumen 14) farther toward the proximal end side than the lateral opening. A wire extending from the proximal end side of the arm is disposed to the cylindrical member P. One end of the wire is connected to part of the area that forms the inside when the second bending part 27 is bent at the outer periphery of the end part of the lateral wall of the cylinder P3, which is disposed to the middle part of the second bending part 27. The other end of the wire is connected to a cartridge 24 such as shown in FIG. 2 and is designed to undergo advancing and retracting action with respect to the arm 20 in response to the operation of the cartridge 24.

In the medical treatment endoscope 80 of this design, once the arm 20 is inserted into the large diameter lumens 13,14, the operator operates the cartridge 24 for manipulating the second bending part 27 at the arm operating portion 30, to pull the wire toward the proximal end side. As a result, the area to which the one end of the wire is connected is pulled toward the proximal end side. At this time, a positional relationship results such that part of the second cylinder P2 is pulled toward the first cylinder P1 side and the cylinders intersect so that the respective axes of the first cylinder P1 and the second cylinder P2 bend. The advance and retraction of the first cylinder P1 on the proximal end side is restricted by the stopper 19 and the groove 22 at the middle openings 17,18. For this reason, the second cylinder P2 is pulled in the direction of the first cylinder P1 as the operator pulls the wire toward the proximal end side, so that the distal end of the second cylinder P2 and the proximal end of the first cylinder P1 move relative to one another in directions that bring them closer together. In this case, the respective axes of the first cylinder P1 and the second cylinder P2 form an angle with respect to the axes of the large diameter lumens 13,14. As a result, the open ends 82a, 82b of the first cylinder P1 and the open end 83 of the second cylinder P2 come into contact with the inner wall of the large diameter lumen 13 at the same time, so that the arm distal end part 21 is fixed in place and supported by the three points 82a, 82b, 83 that are separated with respect to the inner wall of the large diameter lumen. In this way, the first cylinder P1 and the second cylinder P2 are respectively pushed and fixed in place with respect to the large diameter lumen 13 due to the pulling force of the wire, and rotational movement about the axis, and advance and retraction in the axial direction with respect to the large diameter lumens 13,14 of the arm distal end part 21, are restricted.

In this medical treatment endoscope 80, it is possible to prevent movement of the arm 20 in an unintended direction when the operator is treating a target area of treatment by using an endoscopic instrument inserted into the arm 20. Thus, the operator is able to carry out a more precise procedure. Further, the wire for manipulating the second bending part 27 is designed to also be used as the wire that fixes in place the arm 20 with respect to the large diameter lumens 13,14. As a result, the arm 20 can be fixed in place with respect to the large diameter lumens 13,14 without providing a specialized operating system for this purpose. Thus, the design can be simplified and the complexity of the procedure can be reduced.

Note that in this embodiment, a mechanism consisting of a wire for operating the second bending part 27 can be employed for the mechanism for fixing the cylindrical member P in place with respect to the large diameter lumens 13,14. However, the present invention is not limited thereto. A design may also be provided in which the wire for fixing in place the cylindrical member P to the large diameter lumens 13,14 is not also employed as the wire for operating the second bending part 27. Rather, a wire for pulling the second cylinder P2 and a cartridge 24 for operating the wire are provided. In this case, it is not necessary to bend the second bending part 27 for fixing in place the arm 20 to the large diameter lumens 13,14. As a result, with the arm distal end part 21 laying along the central axis of the large diameter lumens 13,14, the arm 20 can be fixed in place to the large diameter lumens 13,14, and the degree of freedom of operation of the arm can be increased.

Next, the seventh embodiment of the present invention will be explained with reference to FIGS. 15 and 16. The medical treatment endoscope 90 according to this embodiment differs from the preceding medical treatment endoscopes with respect to the internal design of the arm distal end part.

Figure 15:
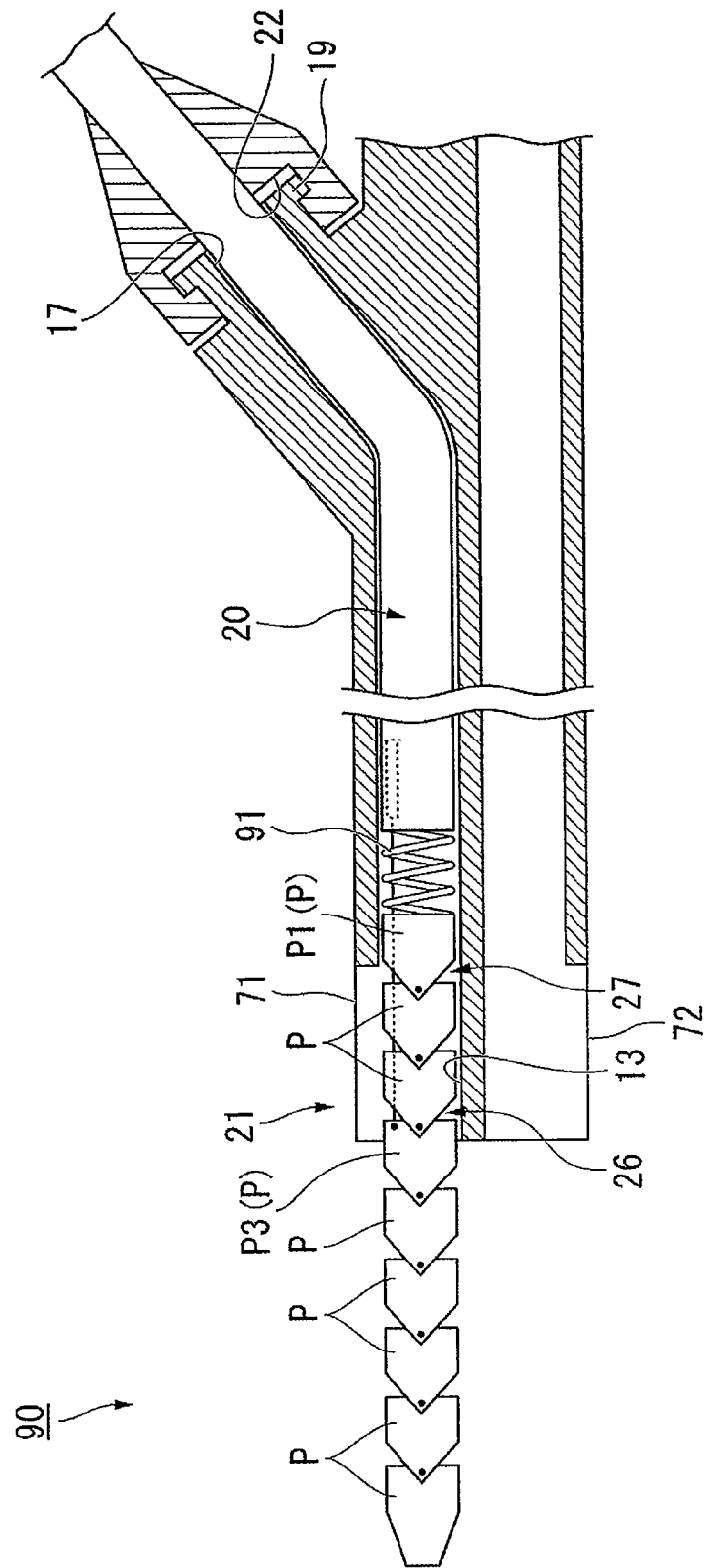
FIG. 15 is a view in partial cross-section of the action during use of the medical treatment endoscope according to a seventh embodiment of the present invention.
Figure 16:
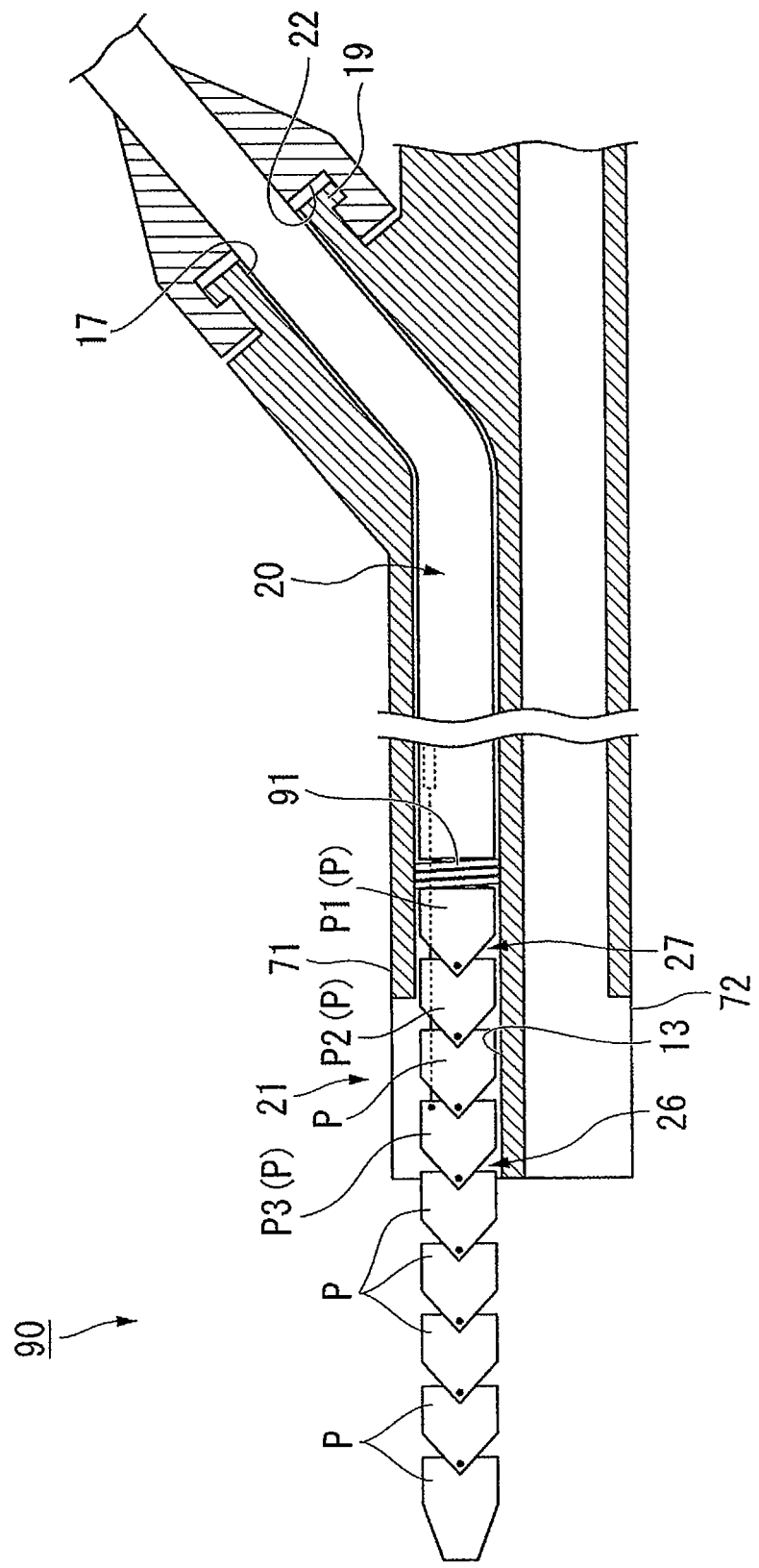
FIG. 16 is a view in partial cross-section of the action during use of the medical treatment endoscope.

As shown in FIGS. 15 and 16, a biasing member 91 is installed to the proximal end side of the first cylinder P1 on the arm distal end part 21. The biasing member 91 is designed to expand in the axial direction of the arm 20. When the biasing member 91 is compressed, it undergoes elastic deformation so that its diameter is larger than when the biasing member 91 is free. In this embodiment, by pulling the wire toward the proximal end side of the arm, the first cylinder P1 comes to lie along the axial line of the arm 20 and is pulled toward the proximal end side of the arm 20.

In the medical treatment endoscope 90 of this design, once the arm 20 is inserted into the large diameter lumen 13 (or the large diameter lumen 14) and the arm distal end part 21 is disposed to the positional relationship in which it projects out from the distal end of the medical treatment endoscope 90, the operator manipulates the cartridge 24 to pull the wire toward the proximal end side of the arm. As a result, one end of the wire pulls the first cylinder P1 toward the proximal end side of the arm 20, compressing the biasing member 91, which expands in the radial direction. The inner wall of the large diameter lumens 13,14 and the biasing member 91 come into contact and the biasing member 91 presses against the inner wall of the large diameter lumens 13,14 in the radial direction. As a result, the biasing member 91 becomes fixed in place with respect to the large diameter lumens 13,14. Next, the operator manipulates the cartridge 24 and pulls the wire toward the proximal end side. The cylinder P3 is pulled toward the proximal end side, and the proximal end of the second bending part 27 bends in the same manner as in the preceding embodiment. As a result, the arm distal end part 21 rotates and moves in the radially outward direction of the medical treatment endoscope 90 via the lateral opening 71 (or the lateral opening 72) of the medical treatment endoscope, employing the connection between the first cylinder P1 and the second cylinder P2 as the center of rotation. As needed, the operator can manipulate the cartridge 24 to bend the distal end of the second bending part 27 in addition to the proximal end of the second bending part 27, and move the arm 20 so that the distal end part 21 of the arm 20 is disposed at the desired position.

This medical treatment endoscope 90 is provided with a design in which the dimensions in the radial direction increase when the biasing member 91 is compressed, causing the biasing member 91 to come into contact with the inner wall surface of the large diameter lumens 13,14. As a result, it is possible to use a simple structure to fix in place the relative position of the arm distal end part 21 with respect to the large diameter lumens 13,14.

Note that the wire which has one end fixed in place to cylinder P3 may be connected to the proximal end of the first cylinder P1. In this case, the arm 20 can be fixed in place with respect to the large diameter lumens 13,14 without bending the second bending part 27.

Next, an eighth embodiment of the present invention will be explained with reference to FIGS. 17 and 18. The medical treatment endoscope 100 according to this embodiment differs from the preceding medical treatment endoscopes with respect to the design of the distal end of the medical treatment endoscope.

Figure 17:
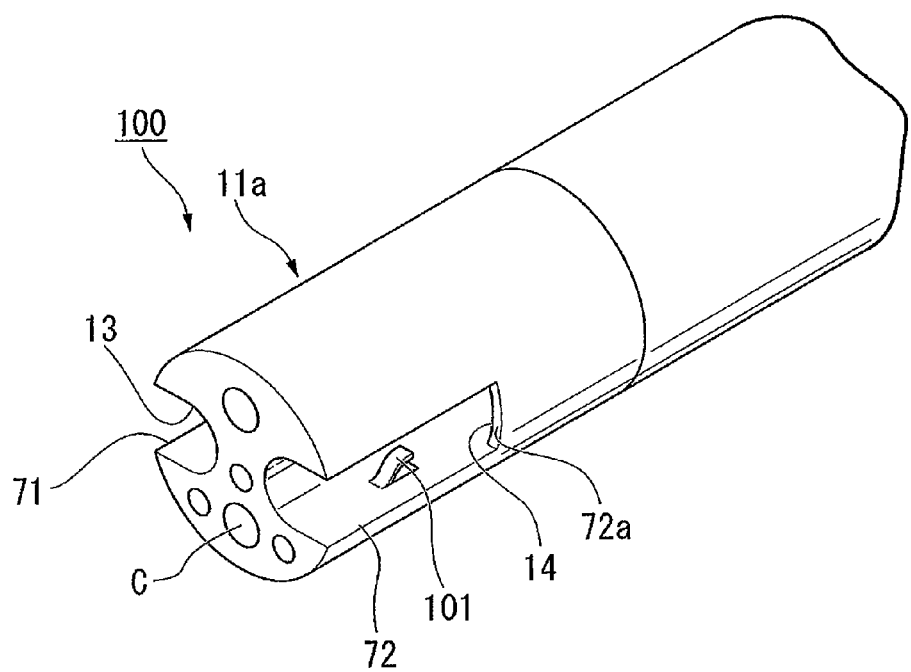
FIG. 17 is an enlarged view showing part of the distal end of the medical treatment endoscope according to an eighth embodiment of the present invention.
Figure 18:
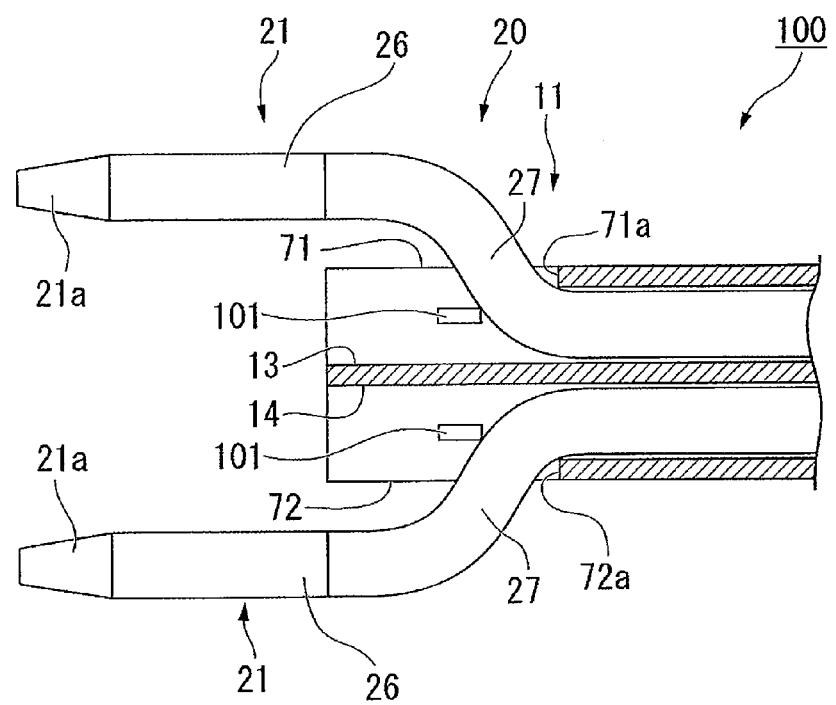
FIG. 18 is a view in partial cross-section of the action during use of the medical treatment endoscope.

As shown in FIGS. 17 and 18, an elastic member 101 is provided to the inner wall of the large diameter lumens 13,14 on the distal end 11a of the medical treatment endoscope 100.

The elastic member 101 of this embodiment is a plate spring. One end of the elastic member 101 is fixed in place to the inner wall of the large diameter lumen 13 (or large diameter lumen 14), and the other end of the elastic member 101 projects out in the radial direction from the large diameter lumens 13,14. The elastic member 101 is disposed to form a positional relationship such that there is a space that permits passage of the arm 20 in between the proximal end of the lateral openings 71,72 on the medical treatment endoscope and the other end of the elastic member 101.

In a medical treatment endoscope 100 of this design, a positional relationship is provided in which the operator inserts the arm 20 into the large diameter lumens 13,14, and the arm distal end part 21 projects out from the distal end 11a of the medical treatment endoscope 100. The tapered part 21a of the arm 20 has a tapered form, so that the tapered portion of the tapered part 21a of the arm 20 comes into contact with the elastic member 101. The other end of the elastic member 101 becomes housed in the inner wall of the large diameter lumens 13,14 in response to the relative movement of the arm 20 toward the distal end side of the medical treatment endoscope 100. Next, the operator manipulates the cartridge 24 which is fixed in place to the arm operating portion 30 and pulls the wire toward the proximal end side, bending the second bending part 27 as a result. When the second bending part 27 bends, the arm distal end part 21 rotates and moves in the radial direction via the lateral opening 71 (or lateral opening 72) of the medical treatment endoscope 100. When the arm distal end part 21 revolves to a position in the space between the proximal end lateral end parts 71a,72a of the lateral openings and the elastic members 101, the pushing force on the elastic member 101 by the arm 20 is released, so that the other end of the elastic member 101 once again projects out in the radial direction of the large diameter lumens 13,14. In this state, the other end of the elastic member 101 comes into contact with the outer peripheral surface of the arm 20 and the movement of the arm 20 along the axis of the large diameter lumens 13,14 toward the distal end is prevented. On the other hand, the outer peripheral surface of the arm 20 comes into contact with the proximal end lateral end parts 71a,72a of the lateral openings 71,72 of the medical treatment endoscope 100, so that movement of the arm 20 along the axis of the large diameter lumens 13,14 toward the proximal end side is prevented by the proximal end lateral end parts 71a,72a. Accordingly, the arm 20 can be fixed in place when it is in a state of insertion into the large diameter lumens 13,14, so that it cannot advance or retract with respect to the medical treatment endoscope 100.

Next, a ninth embodiment of the present invention will be explained with reference to FIGS. 19 through 21. The medical treatment endoscope 110 according to this embodiment differs from the preceding medical treatment endoscopes with respect to the shape of the arm and the structure of the distal end of the medical treatment endoscope.

Figure 19:
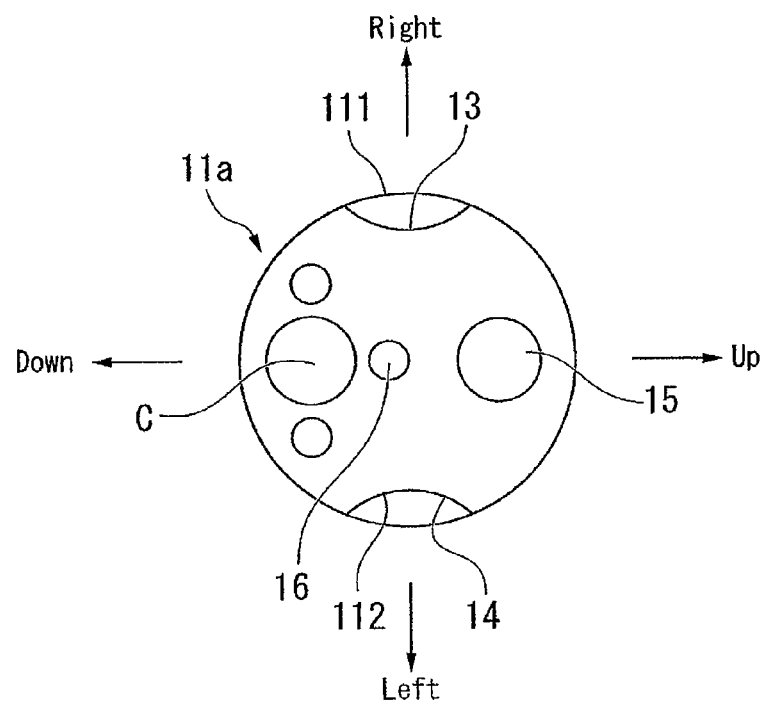
FIG. 19 is an enlarged view showing part of the distal end of the medical treatment endoscope according to a ninth embodiment of the present invention.
Figure 20:
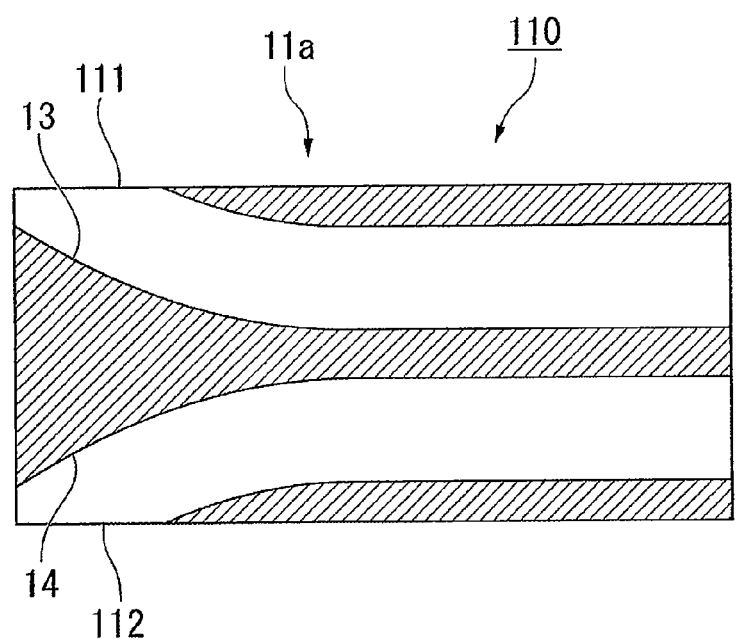
FIG. 20 is a cross-sectional view showing part of the distal end of the medical treatment endoscope.

As shown in FIGS. 19 and 20, at the distal end 11a of the medical treatment endoscope 110, the large diameter lumens 13,14 bend in the radial direction approaching the proximal end side to the distal end side of the medical treatment endoscope 110, and have end openings 111,112 which open in the lateral direction at the distal end of the medical treatment endoscope 110. An image capturing mechanism C is disposed at a position below the large diameter lumens 13,14 as indicated by the arrow marked "Down" in the figure. In this embodiment, a bending tendency is provided to the arm distal end part 21 (see FIG. 21). The form of the bend of the arm distal end is roughly the same as the form of the bend in the large diameter lumen.

Figure 21:
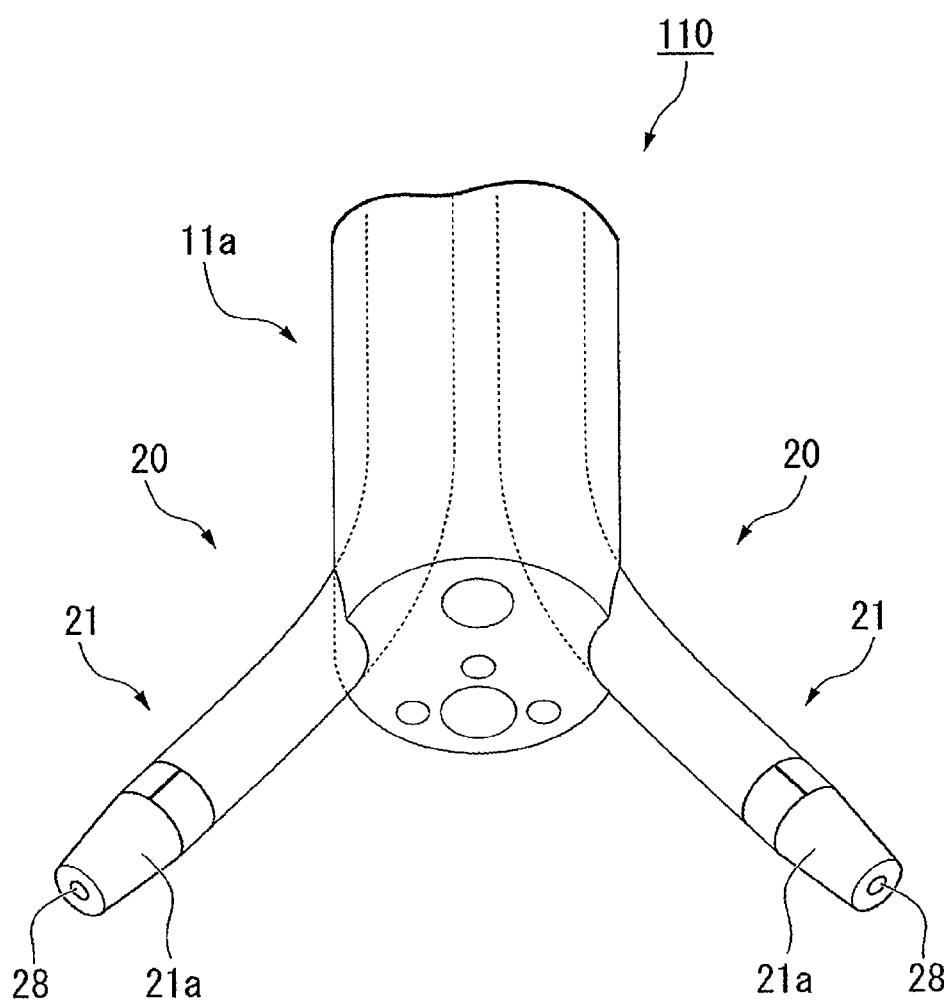
FIG. 21 is a view showing the action during use of the medical treatment endoscope.

As shown in FIG. 21, the arms 20 which are inserted from the middle openings 17,18 of the insertion portion 11 into the large diameter lumens 13,14 in a medical treatment endoscope 110 of this design, are moved to the distal end by pushing. Next, the operator projects the arms 20 out from the distal end of the medical treatment endoscope 110 via the inside of the large diameter lumens 13,14. At this time, the arms 20 undergo relative rotation about the axis within the large diameter lumens 13,14, and the bending tendency that is provided to the arms 20 and the direction of bending that is provided to the large diameter lumens 13,14 match.

Since a bending tendency is imparted to the arms 20, the tapered part 21a of the arm 20 moves away from the center axis of the medical treatment endoscope 110 in the radial direction as the tapered part 21a is projected from the distal end of the medical treatment endoscope. In other words, the respective distal ends of the arms 20 that are inserted into the large diameter lumens 13,14 so as to form a right and left pair, move away from one another in the radial direction with respect to the center axis of the medical treatment endoscope 110. Thereafter, the first bending part 26 or the second bending part 27 are bent in the same manner as in the preceding embodiments, and the position of the distal end of the arms 20 is adjusted to a suitable position. An endoscopic instrument is then inserted into the medical treatment lumen 28 of the arm 20 and the appropriate procedure is carried out.

In this medical treatment endoscope, the inclination of the arm 20 can be positioned by means of a simple structure. Further, a bending tendency is provided to the arm distal end part 21 which moves it away in the radial direction with respect to the central axis of the insertion portion 11. As a result, a design is achieved in which the shape of the bending tendency is adjusted to make the arm distal end part 21 bend in the same manner as the second bending part 27, so that a second bending part 27 need not be provided.

Next, a tenth embodiment of the present invention will be explained with reference to FIGS. 22 and 23. The medical treatment endoscope 120 according to this embodiment differs from the preceding medical treatment endoscopes with respect to the cross-sectional shape of the large diameter lumen and the shape of the arm distal end part.

Figure 22:
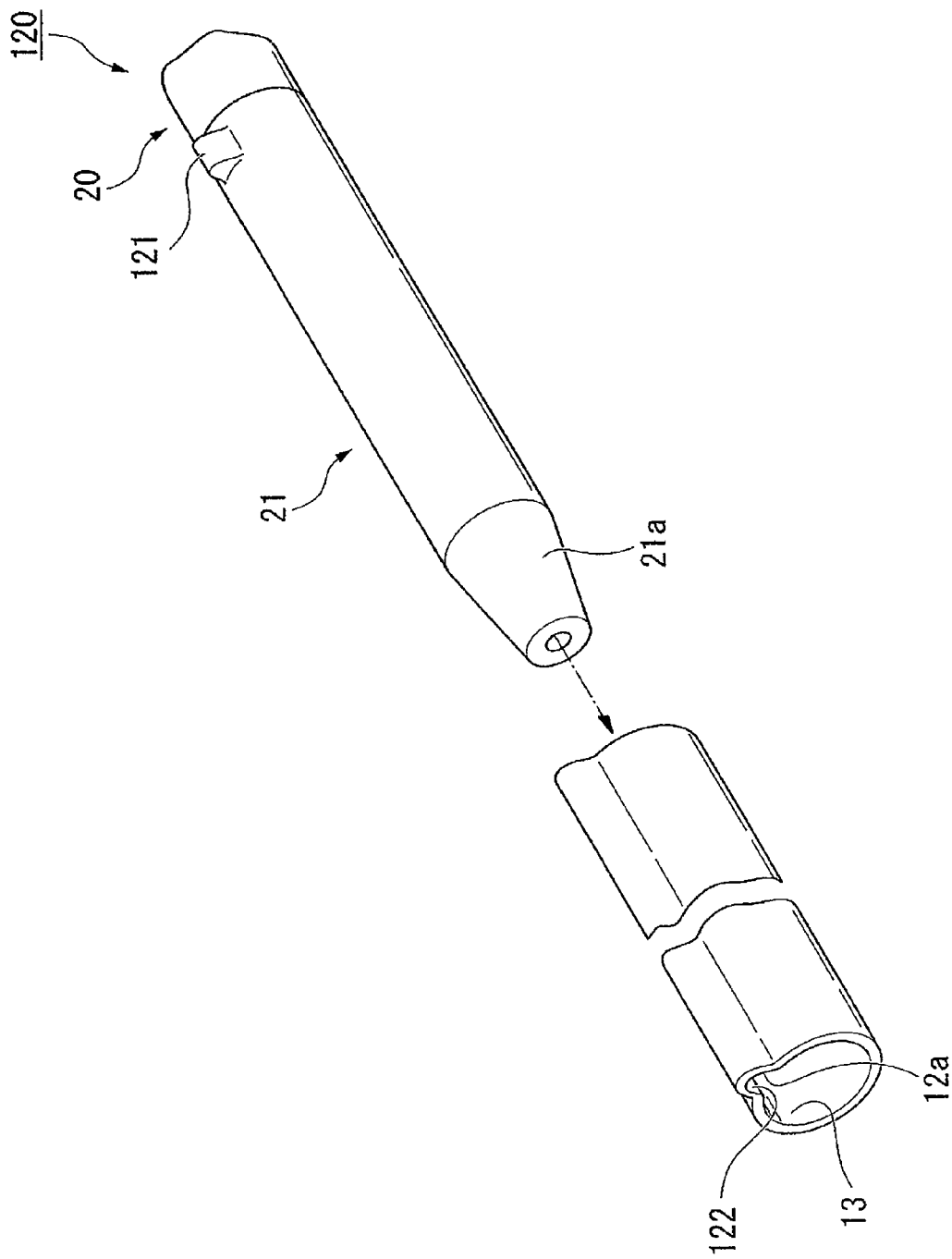
FIG. 22 is a view showing the structure of the distal end of the medical treatment endoscope according to a tenth embodiment of the present invention.

As shown in FIG. 22, an expanded part 121 which expands in the radially outward direction from a portion of the outer peripheral surface is formed to the arm distal end part 21. The shape in radial cross-section of the large diameter lumen 13 (or large diameter lumen 14) is non-circular in this embodiment. A groove 122 that is parallel to the axial line and which can engage with the expanded portion 121 is formed to the large diameter lumens 13,14. The groove 122 is formed to be continuous from the middle openings 17,18 of the large diameter lumens 13,14 to the distal end.

In this medical treatment endoscope 120, when the operator is inserting the arm 20 from the middle openings of the medical treatment endoscope, the position of the arm 20 and the large diameter lumens 13, 14 are aligned along the circumference so as to form a positional relationship in which the expanded part 121 and the groove 122 engage, after which the arm 20 is inserted into the large diameter lumens 13,14. The arm distal end part 21 is supported by the expanded part 121 while being projected out from the distal end of the medical treatment endoscope 120. In this case, the arm distal end part 21 is positioned about the circumference by the engagement of the expanded part 121 and the groove 122, and supported at this position.

In the medical treatment endoscope 120, the arm 20 can be guided to the distal end of the medical treatment endoscope 120 without being twisted about the axis with respect to the large diameter lumens 13,14. Further, since the arm 20 is not twisted around the axis, it is possible to avoid changes in the opening/closing orientation of the distal end of an endoscopic instrument that is inserted into the instrument lumen 28 of the arm 20, so that the endoscopic instrument can be disposed with a suitable positional relationship.

Figure 23:
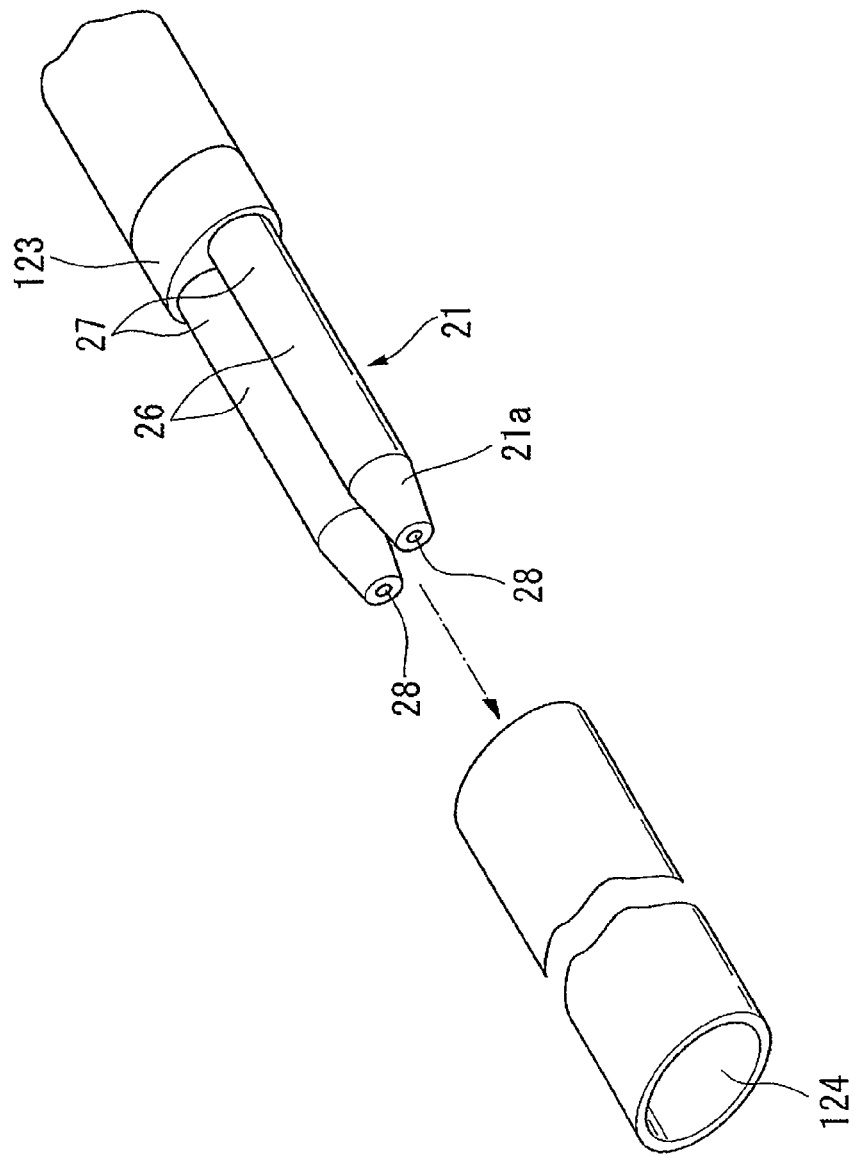
FIG. 23 is a view showing a modification of the medical treatment endoscope.

Note that the design shown in FIG. 23, in which a connecting ring 123 which connects the two arms 20 is formed to the arm distal end part 21, may be provided as a modification of the design shown in FIG. 22. In this embodiment, the two large diameter lumens communicate in a unitary manner. In other words, the large diameter lumen is provided with a single lumen 124 having a shape in radial cross section in which two large diameter lumens 13,14 are separated and wall portions are cut out. Note that even in the case of a shape in which just a portion of the wall is cut out, provided that the two large diameter lumens communicate in the axial direction, then the cross-sectional shape may assume a suitable shape such as a cocoon-like or an elliptical shape. Further, the connecting ring 123 may have a design that encircles the arm 20 at least the proximal end of the second bending part 27 at the arm distal end part 21. It is also acceptable to encircle the entirety of the arm 20 to the proximal end side of the second bending part 27, or to encircle only a part of the arm 20.

Next, an eleventh embodiment of the present invention will be explained with reference to FIG. 24. The medical treatment endoscope 130 according to this embodiment differs from the preceding medical treatment endo scope 1 with respect to the design of the arm distal end and the design of the large diameter lumen on the distal end of the medical treatment endoscope.

Figure 24:
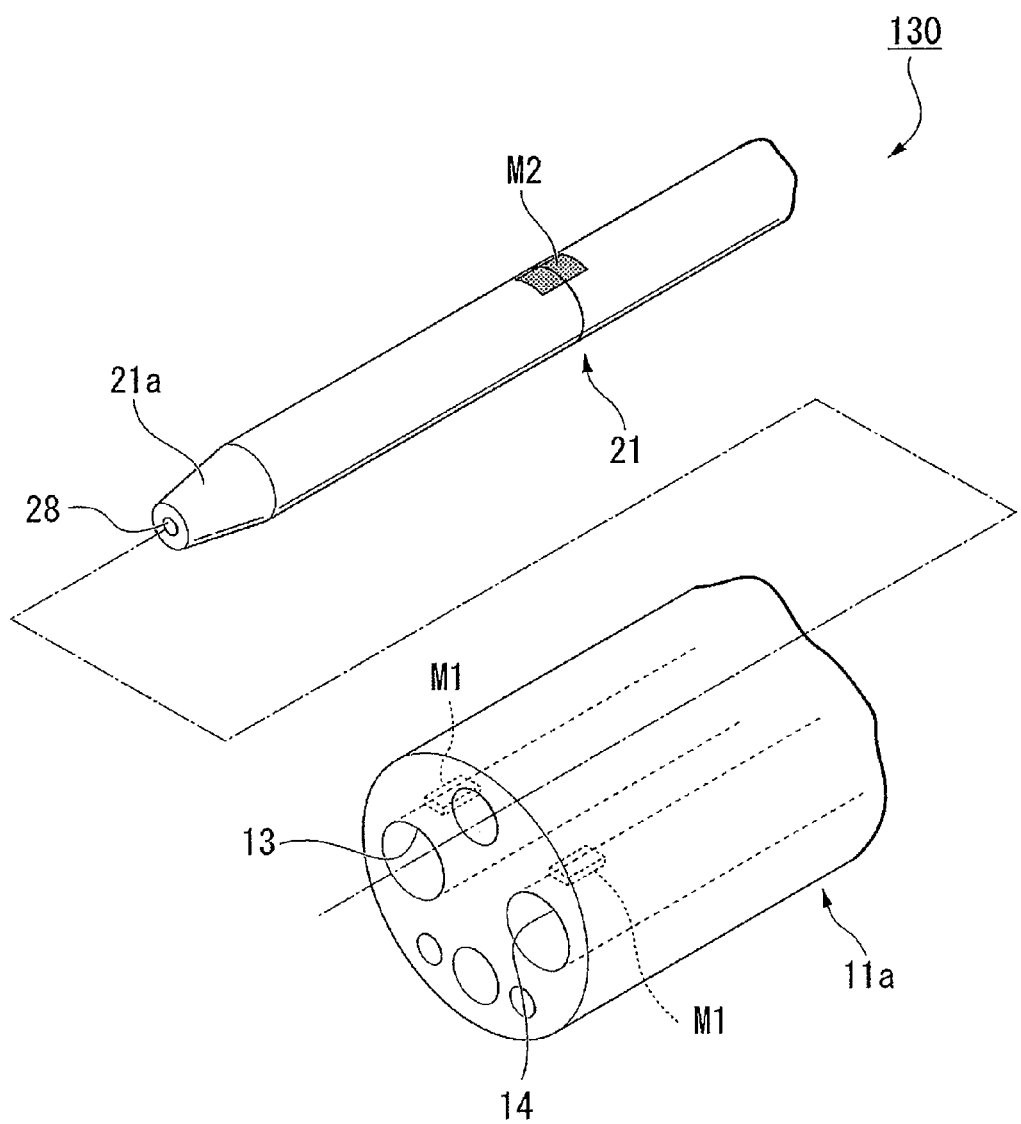
FIG. 24 is a view showing the distal end of the medical treatment endoscope according to an eleventh embodiment of the present invention.

As shown in FIG. 24, an electromagnet M1 is disposed at a specific position on the circumference of the respective inner peripheral surfaces of the large diameter lumens 13,14 at the distal end of the medical treatment endoscope 130. An electromagnet M1 is disposed at one site with respect to each of the large diameter lumens 13,14. In addition, the electromagnets M1 are disposed at equivalent positions on the respective circumferences of the two large diameter lumens 13,14. A magnetic body M2 is provided to one site on the outer peripheral surface of the arm distal end part 21. In this embodiment, the positional relationship of the electromagnet M1 and magnetic body M2 about the axis is such that the respective arms 20 separate in the radial direction with respect to the center line of the two large diameter lumens 13,14 when the second bending part 27 is bent at the arm distal end part 21. Note that other positional relationships are acceptable depending on the arm being used.

In the medical treatment endoscope 130, the electromagnet M1 is prepared in advance by passing a current through it to magnetize it. The operator inserts the tapered part 21*a* of the arm 20 from the middle openings 17,18 of the medical treatment endoscope 130 to the large diameter lumens 13, 14. Next, the tapered part 21*a* of the arm 20 is projected out from the distal end of the medical treatment endoscope 130. Since the operator does not determine the rotational position of the arm 20 about the axis, the position of the magnetic body M2 which is provided to the distal end of the arm 20 and the electromagnet M1 which is provided to the large diameter lumens 13,14 coincide along the axial direction, but the position along the circumference can be optionally determined. Since an attraction is generated that pulls the magnetic body M2 toward the electromagnet M1, the magnetic body M2 is drawn in the direction of the magnet. At this time, the arm 20 is supported on the inner peripheral surface of the large diameter lumens 13,14 in a freely advancing, retracting and rotating manner, so that the electromagnet M1 and the magnetic body M2 rotate about the axis of the arm 20. By bringing the position of the magnetic body M2 and the electromagnetic M1 maximally close, the rotation of the arm 20 about the axis is stopped. As a result, the rotational position of the arm 20 and the large diameter lumens 13, 14 about the circumference is determined and maintained.

In this medical treatment endoscope 130, even if the arm 20 is inserted into the large diameter lumens 13,14 without aligning in the circumferential direction, positioning can be performed by rotating and moving the arm distal end part 21 about the axis on the distal end 11*a* of the medical treatment endoscope 130 due to the electromagnet M1 drawing the magnetic body M2 closer. As a result, the complexity of the positioning procedure can be reduced. In addition, since the arm 20 and the large diameter lumens 13,14 are fixed in place at the position to which the electromagnet M1 draws the magnetic body M2, it is possible to fix in place the relative position of the arm 20 with respect to the large diameter lumens 13,14 along the axial direction.

Next, the twelfth embodiment of the present invention will be explained with reference to FIGS. 25 through 32. The medical treatment endoscope 140 according to this embodiment differs from the preceding medical treatment endoscopes with respect to the design of the distal end of the large diameter lumen and the arm distal end.

Figure 25:
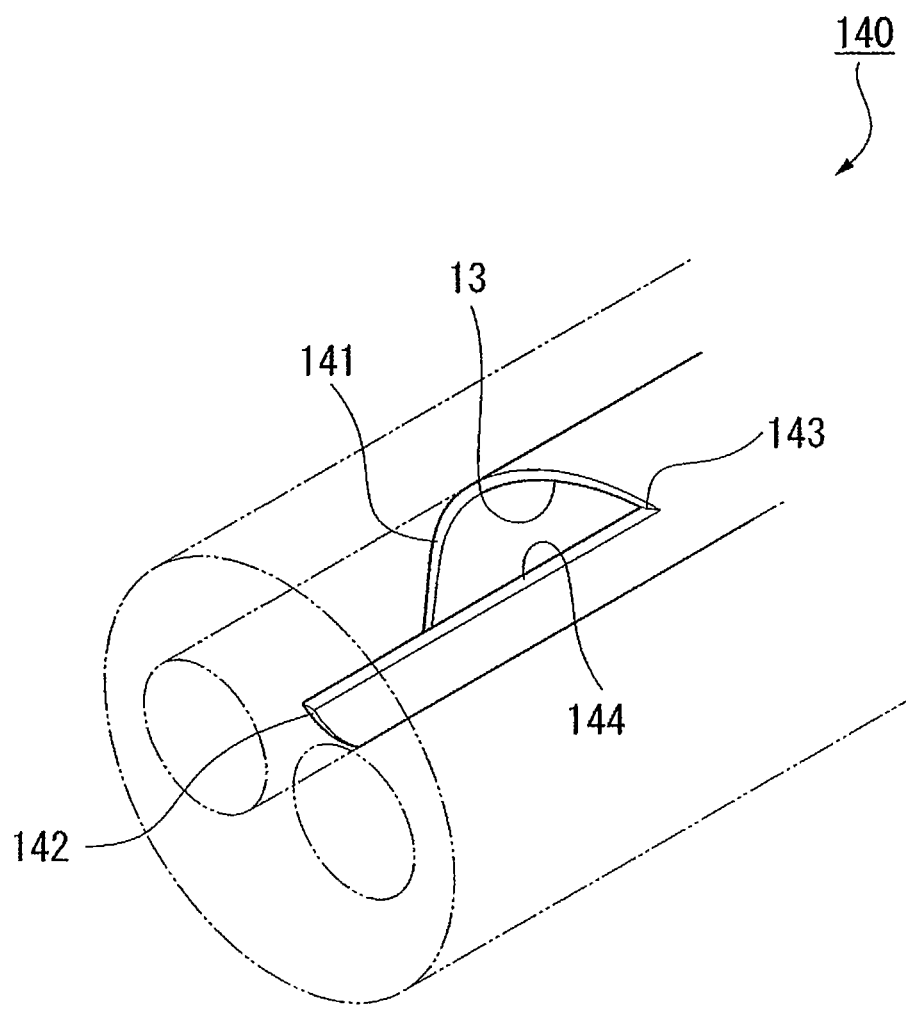
FIG. 25 is a view showing part of the distal end of the medical treatment endoscope according to a twelfth embodiment of the present invention.

As shown in FIG. 25, in the medical treatment endoscope 140 according to this embodiment, a helical end surface 141 is formed on the distal end to the large diameter lumen 13 (or the large diameter lumen 14) and runs clockwise when viewed from the distal end side. The helical end surface 141 is formed over a single circumference about the periphery, and is formed to have a specific length in the axial direction. The distal end side end 142 and the proximal end lateral end part 143 of the helical end surface 141 are parallel to the axis of the large diameter lumen, and a lateral cross-section 144.

Figure 26:
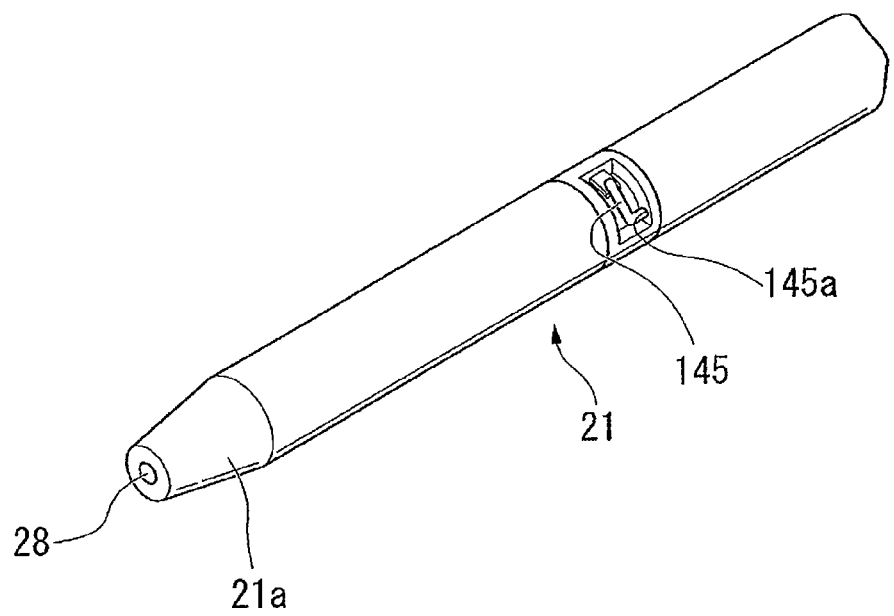
FIG. 26 is an enlarged view showing the arm distal end of the medical treatment endoscope.

As shown in FIG. 26, the outer peripheral surface of the arm distal end part 21 is provided with a cam pin 145 in which one end 145*a* is supported by the outer peripheral surface of the arm distal end part 21 and which can undergo rotational movement employing one end 145*a* as the rotational center; and a biasing member 146 which biases the cam pin 145 in the radially outward direction on a portion of the outer peripheral surface of the arm distal end part 21.

Figure 27:
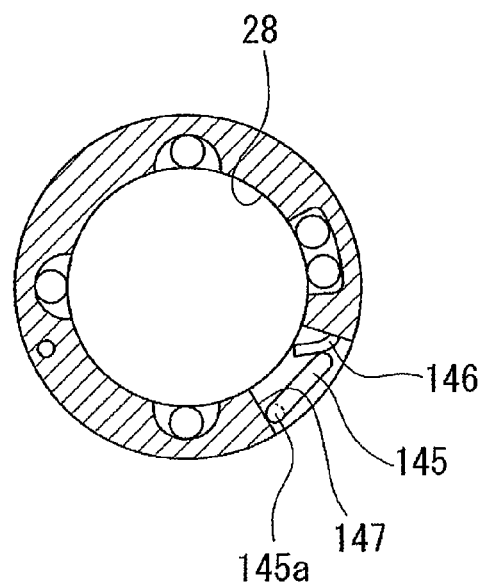
FIG. 27 is a view in partial cross section showing the action of the cam pin of the medical treatment endoscope.
Figure 28:
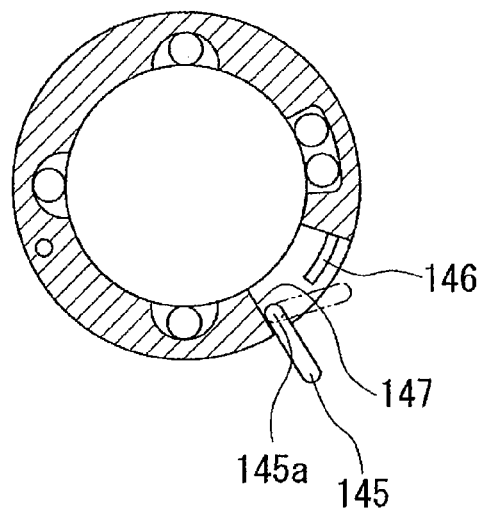
FIG. 28 is a view in partial cross section showing the action of the cam pin of the medical treatment endoscope.

As shown in FIGS. 27 and 28, a movement controlling part 147 is formed to the outer peripheral surface of the arm distal end part 21 for controlling the rotational movement of the cam pin 145 by coming in contact with the outer peripheral surface of the cam pin 145. The center axis of rotation of the cam pin 145 is one end 145*a* thereof. One end 145*a* is parallel to the axis of the arm 20. The cam pin 145 has a positional relationship such that the projecting portion when cam pin 145 is rotated and moved in the radially outward direction can contact the spiral end surface 141, and the cam pin 145 does not contact the inner surface of the large diameter lumens 13,14 when the cam pin 145 is positioned farther distally than the distal end side end 142 of the spiral end surface 141.

In a medical treatment endoscope 140 of this design, the operator first inserts the tapered part 21*a* of the arm 20 from the middle openings 17,18 of the medical treatment endoscope 140 into the large diameter lumens 13,14. At this time, the cam pin 145 which is disposed to the tapered part 21*a* of the arm 20 is biased toward the radially outward direction of the arm distal end part 21, so that the cam pin 145 is pushed into the radially inward direction of the arm distal end part 21, and the arm distal end part 21 is inserted into the middle openings 17,18.

Figure 29:
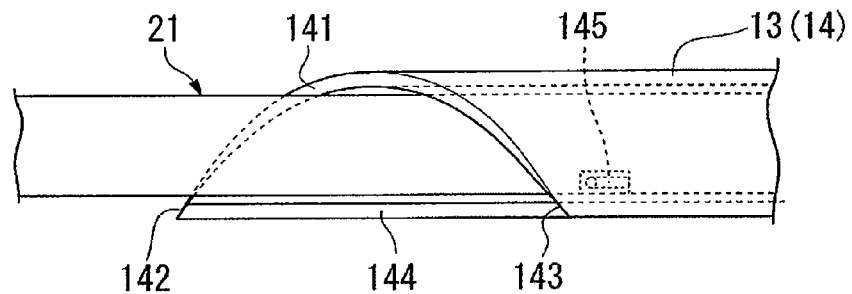
FIG. 29 is a view showing the action during use of the medical treatment endoscope.

As shown in FIG. 29, the cam pin 145 is supported on the inner peripheral surface of the large diameter lumens 13,14. In this state, the advance and retraction of the arm 20 with respect to the large diameter lumens 13,14 is not hindered.

Figure 30:
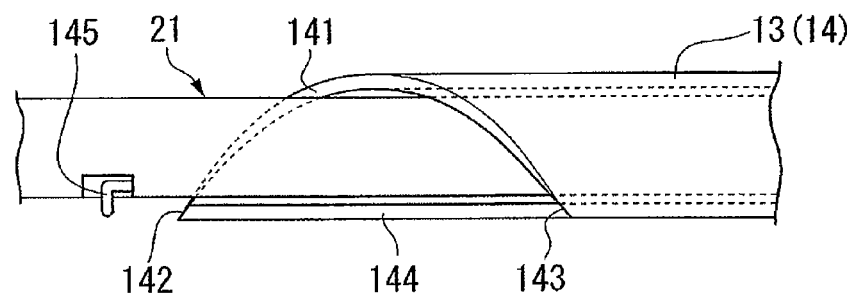
FIG. 30 is a view showing the action during use of the medical treatment endoscope.

As shown in FIG. 30, the tapered part 21a of the arm 20 projects out from the distal end of the large diameter lumens 13,14. In the arm distal end part 21, when the position of the cam pin 145 which lies along the axis of the large diameter lumens 13,14 is moved farther toward the distal end side than the distal end of the large diameter lumens 13,14, the cam pin 145 is projected in the radially outward direction from the arm distal end part 21 by the biasing member 146. Next, the operator pulls the arm 20 toward the proximal end side with respect to the medical treatment endoscope 140. As a result, the cam pin 145 is pulled toward the proximal end side with respect to the large diameter lumens 13,14, and comes into contact with a portion of the helical end surface 141. When the operator pulls the arm 20 farther toward the proximal end side with respect to the large diameter lumens 13,14, the cam pin 145 moves toward the proximal end side while rotating clockwise as seen from the distal end side along the helical end surface 141, about the axis of the arm 20. As this time, the cam pin 145 receives a force from the helical end surface 141 in the direction which opens the cam pin 145 in the radially outward direction of the arm 20. Accordingly, the cam pin 145 does not bend in the radially inward direction of the arm 20. The arm distal end part 21 also rotates in the clockwise manner about the axis at this time.

Figure 31:
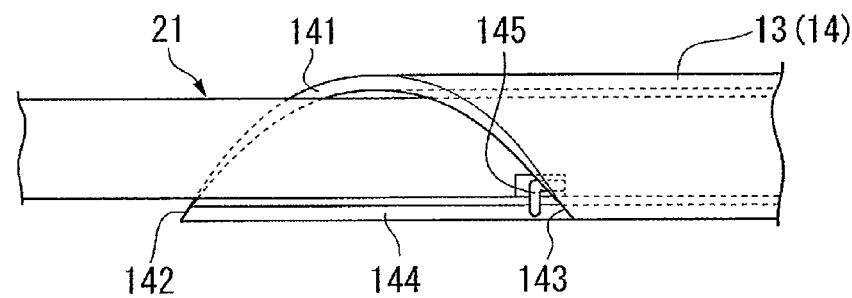
FIG. 31 is a view showing the action during use of the medical treatment endoscope.

As shown in FIG. 31, the cam pin 145 reaches the proximal end lateral end part 143 of the helical end surface 141, and comes into contact with the lateral cross section 144. By pulling the arm 20 toward the proximal end side, the operator generates a pulling force on the cam pin 145 toward the proximal end side. However, since the cam pin 145 is supported by the proximal end side 143, the arm 20 cannot move farther toward the proximal end side. At this time, the cam pin 145 is positioned at the proximal end lateral end part 143, so that the arm distal end part 21 and the large diameter lumens 13,14 are held in a specific positional relationship about the axis. Thereby, the positional relationship between the arm 20 and each of the large diameter lumens 13, 14 is determined about the circumferential direction and in the axial direction.

Figure 32:
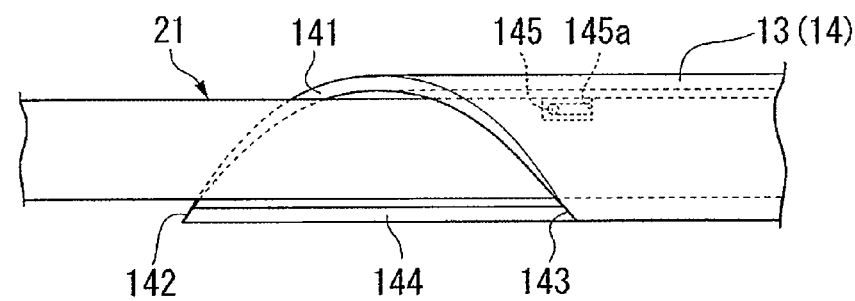
FIG. 32 is a view showing the action during use of the medical treatment endoscope.

As shown in FIG. 32, when removing the arm 20 from the large diameter lumens 13,14, the arm 20 is rotated with respect to the large diameter lumens 13,14 clockwise about the axis as seen from the distal end. As a result, the cam pin 145 is subjected to a pressing force by the lateral cross section 144, and moves rotationally centered about one end 145a, to be housed inside the outer wall portion of the arm distal end part 21. By pulling the arm 20 toward the proximal end side of the large diameter lumen in this state, the arm 20 is withdrawn from the large diameter lumens 13,14.

In this medical treatment endoscope 140, when the arm 20 is pulled toward the proximal end, the helical end surface 141 functions as an inclined cam surface for guiding the cam pin 145. The cam pin 145 is guided by the helical end surface 141 and is positioned at the proximal end lateral end part 143. At the proximal end lateral end part 143, the cam pin 145 is in a state of contact with the lateral cross section 144, and rotation about the axis in a clockwise manner as viewed from the proximal end side and distal end side is prevented. For this reason, it is possible to determine the positional relationship between the arm 20 and each of the large diameter lumens 13,14 about the circumferential direction and in the axial direction at a same time. As a result, it is possible to highly precisely position the arm distal end part 21 to the treatment endoscope.

In addition, since the positional relationship between the arm distal end part 21 and each of the large diameter lumens 13, 14 is determined about circumferential direction and in the axial direction at the same time, it is possible to coincide accurately the relationship between the operation of the arm operating portion 30 and the direction of the movement of the arm distal end portion 21.

Conventionally, particularly in the case of the large-sized arm operating portion 30, it was difficult to accurately recognize the corresponding relationship between the operational direction of the arm operating portion and the bending direction of the arm. However, in the medical treatment endoscope 140 according to this embodiment, since the positioning relationship between the arm distal end portion 21 and the large diameter lumens 13, 14 is determined about the circumferential direction and in the axial direction as described above, even when the arm operating portion 30 is manipulated on the basis of the image of the target portion obtained by the image capturing mechanism C in the state where the positional relationship between the arm distal end portion 21 and the large diameter lumens 13, 14 is not visually recognized, the operator is able to operate the arm distal end portion 21.

In addition, since it is possible to position the arm distal end portion 21 to each of the large diameter lumens 13, 14, when the second bending part 27 is bent, two arms 20 reliably move in a direction away from each other. For this reason, it is possible to obtain the positional relationship (tri-angulation), which facilitates the treatment and maintains an appropriate gap between two arms 20, by means of the arm distal end portion 21.

Further, since the positional relationship between the arm 20 and each of the large diameter lumens 13,14 is determined in the arm distal end portion 21, even when the arm 20 on the proximal end side of the arm distal end portion 21 is twisted in the inside of each of the large diameter lumens 13,14, it is possible to uniformly maintain the positional relationship between the arm distal end portion 21 and each of the large diameter lumens 13,14.

Conventionally, in the case of the above-described twisting action, the curve direction of the arm was changed during the treatment even when performing the same manipulation on the observation image. Accordingly, it was difficult to perform the manipulation intuitively.

In the medical treatment endoscope 140 according to this embodiment, since it is possible to uniformly maintain the positional relationship between the arm distal end portion 21 and each of the large diameter lumens 13 and 14, it is possible to optimally maintain the bending direction of the arm during the treatment, and thus for the operator to perform intuitive manipulation of the arm distal end portion 21 on the basis of the image obtained by the image capturing mechanism C.

Next, a thirteen embodiment of the present invention will be explained with reference to FIGS. 33 through 35. The medical treatment endoscope 150 according to this embodiment differs from the preceding medical treatment endoscopes with respect to the design of the arm distal end and the distal end of the medical treatment endoscope.

Figure 33:
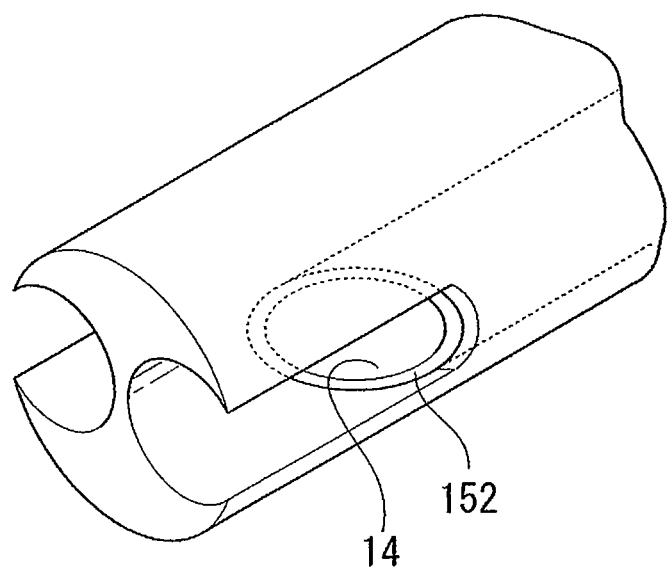
FIG. 33 is a view showing part of the distal end of the medical treatment endoscope according to a thirteenth embodiment of the present invention.
Figure 34A:
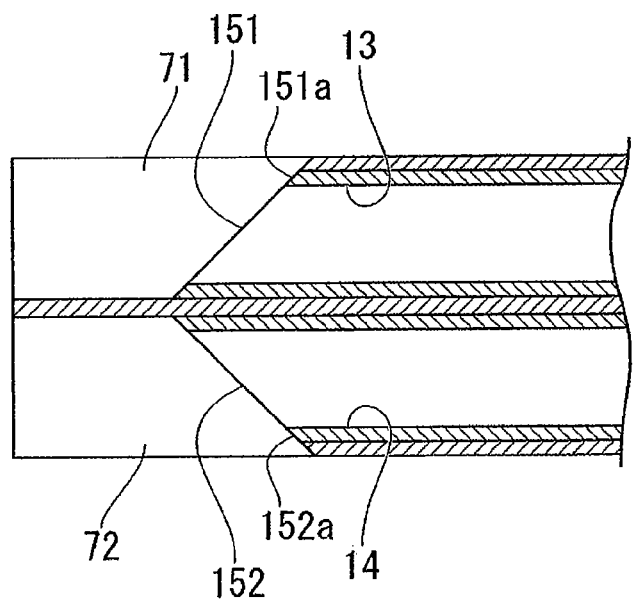
FIG. 34A is a cross-sectional view showing part of the distal end of the medical treatment endoscope.

As shown in FIGS. 33 and 34A, in the medical treatment endoscope 150 according to this embodiment, the distal end of the large diameter lumens 13,14 form inclined end surfaces 151,152 which form an angle with respect to the central axis. Lateral openings similar to the lateral openings 71,72 described above are formed to the medical treatment endoscope 150 to a position which is at least farther forward than the large diameter lumens 13,14.

Figure 35:
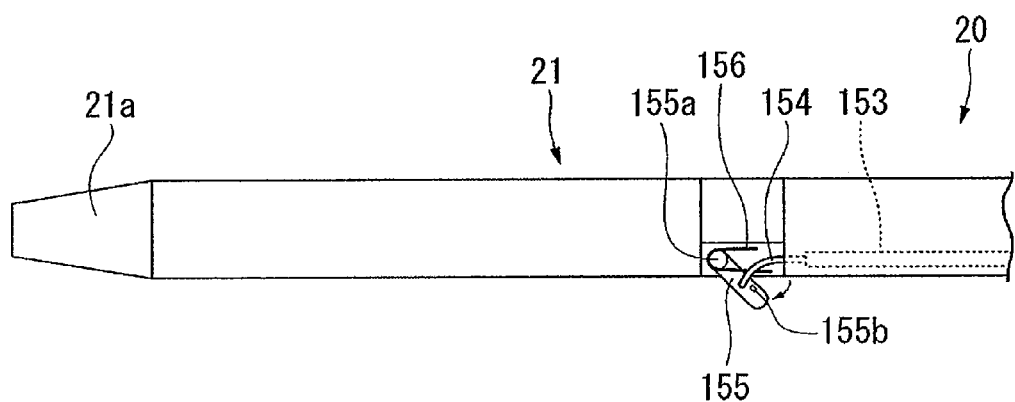
FIG. 35 is a view showing the arm distal end of the medical treatment endoscope.

As shown in FIG. 35, a cam pin 155 is provided to the arm distal end part 21. One end 155a of cam pin 155 is supported by the outer peripheral surface of the arm distal end part 21, with cam pin 155 undergoing rotational movement centered about this end 155a. A torsion spring 156 is wound around the end 155a of the cam pin 155. One end of the torsion spring 156 contacts the outer peripheral surface of the arm and the other end of the torsion spring 156 biases a projection 155b formed to the middle part of the cam pin 155 in the radially outward direction. One end of a wire 154 is connected to the cam pin 155, with the wire 154 inserted into a coil sheath 153 provided inside the lateral wall of the arm 20 and extending toward the proximal end side. The wire 154 projects out from the proximal end side of the arm 20 and is guided to the arm operating portion 30.

In the medical treatment endoscope 150 of this design, the operator inserts the arm 20 from the middle openings 17,18 into the large diameter lumens 13,14. Next, the tapered end 21a of the arm 20 is projected out form the distal end of the large lumens 13,14. When the position of the cam pin 155 lying along the axis of the large diameter lumens 13,14 at the arm distal end part 21 moves more distally than the distal end of the large diameter lumens 13,14, the cam pin 155 undergoes rotational movement so as to project in the radially outward direction from the arm distal end part 21 by means of the torsion spring 156 (see the arrow in FIG. 35). Next, the operator pulls the arm 20 toward the proximal end side with respect to the large diameter lumens 13,14. As a result, the cam pin 155 is pulled toward the proximal end side with respect to the large diameter lumens 13,14, and comes into contact with a portion of the inclined end surface 151,152. When the operator pulls the arm 20 further toward the proximal end side with respect to the large diameter lumens 13,14, the cam pin 155 moves along the inclined end surfaces 151, 152 toward the proximal end side while rotating clockwise or counter clockwise about the arm axis as seen from the distal end. The arm distal end part 21 also rotates about the axis at this time. The cam pin 155 reaches the proximal end lateral end parts 151a,152a of the inclined end surfaces 151,152. By pulling the arm 20 toward the proximal end side, the operator also generates a pulling force on the cam pin 155 toward the proximal end side. However, since the arm 20 is supported by the proximal end lateral end part 151a,152a, it does not move farther toward the proximal end side. For this reason, the position of rotation about the circumference of the arm distal end part 21 is determined to be a specific rotational position at which the cam pin 155 is located at the proximal end lateral end parts 151a,152a of the inclined end surfaces 151,152. Thereby, the positional relationship between the arm 20 and each of the large diameter lumens 13 and 14 is determined about the circumferential direction and in the axial direction.

When withdrawing the arm 20 from the large diameter lumens 13,14 once the procedure is completed, the contact between the cam pin 155 and the inclined end surfaces 151, 152 is released by moving the arm 20 to the distal end side of the large diameter lumens 13,14. The wire 154 is then pulled toward the proximal end side of the arm 20. As a result, the cam pin 155 is pulled by the wire 154, and one end 155a undergoes rotational movement in the radially inward direction about the rotational center. With the cam pin 155 housed inside the lateral wall of the arm distal end part 21 in this way, the arm 20 is withdrawn from the large diameter lumens 13,14 by pulling the arm 20 toward the proximal end side of the large diameter lumens 13,14 while pulling the wire 154 toward the proximal end side of the arm 20.

In this embodiment, the inclined end surfaces 151,152 function as an inclined cam surface for guiding the cam pin 155. The cam pin 155 is guided by the inclined end surfaces 151,152, and is positioned on the proximal end lateral end parts 151a,152a. As a result, the rotational position of the arm 20 about the axis can be positioned and fixed in place with respect to the medical treatment endoscope 150. Further, as compared to the medical treatment endoscope 140 according to the twelfth embodiment, it is possible to roughly halve the length of the inclined cam surface in the axial direction. As a result, the distal end of the medical treatment endoscope 150 can be made more compact.

Figure 34B:
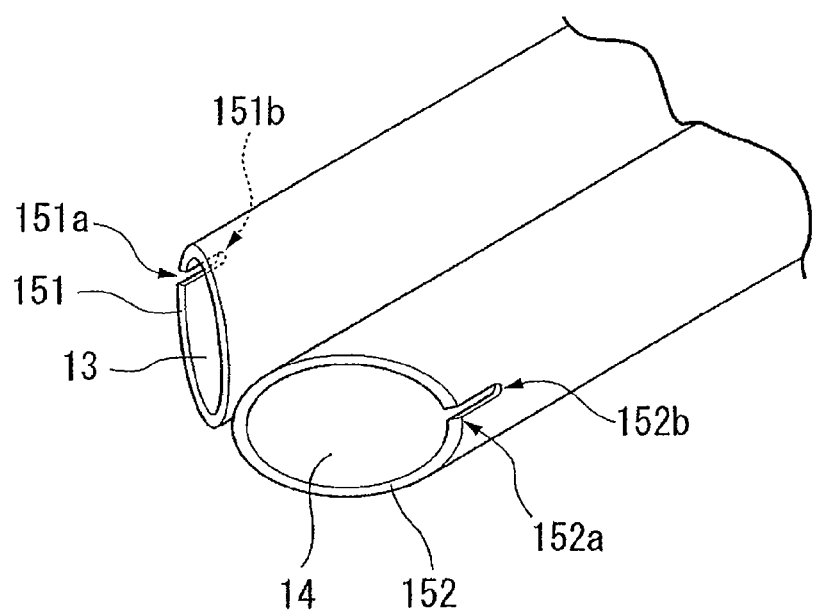
FIG. 34B is a perspective view showing a configuration of a modified example of the medical treatment endoscope.

In addition, as shown in FIG. 34B, the large diameter lumens 13,14 may be respectively provided with notch portions 151b and 152b which further extend from the proximal end side ends 151a and 152a of the inclined end surfaces 151 and 152 to the proximal ends thereof. In this case, when the cam pin 155 is fitted to each of the notch portions 151b and 152b, it is possible to highly precisely position the cam pin 155 about the axis of each of the large diameter lumens 13,14.

Further, even when an external force is applied to the arm 20 or each of the large diameter lumens 13,14 so that the arm 20 rotates with respect to each of the large diameter lumens 13,14, since the cam pin 155 reliably engages with each of the notch portions 151b,152b, it is possible to reliably fix the arm 20 and the large diameter lumens 13,14.

Next, the fourteenth embodiment of the present invention will be explained with reference to FIGS. 36 through 38. The medical treatment endoscope according to this embodiment differs from the preceding medical treatment endoscope 1 with respect to the provision of an attachment to the distal end of the medical treatment endoscope and in the design of the arm distal end.

Figure 36:
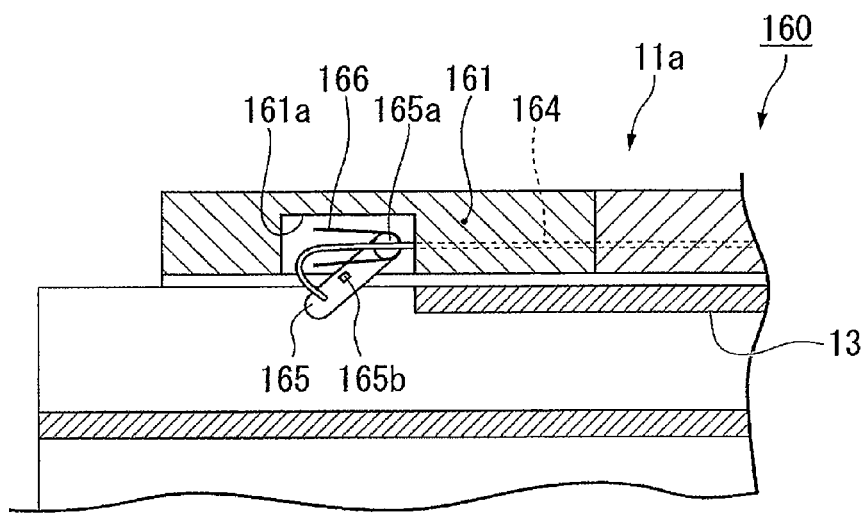
FIG. 36 is a view in partial cross-section showing the distal end of the medical treatment endoscope according to a fourteenth embodiment of the present invention.

As shown in FIG. 36, the medical treatment endoscope 160 has a freely attaching and releasing attachment 161 on the distal end 11a. Concavities 161a,161b (not shown in the figures) are formed to two opposing sites on the inside of the attachment 161. A cam pin 165 is provided to the inside of the concavities 161a,161b. On end 165a is supported by the concavities 161a,161b, with the cam pin 165 undergoing rotational movement in the radially inward direction employing the one end as the rotational center. A torsion spring 166 is wound about one end 165a of the cam pin 165, and the projection 165b which is formed to the middle part of the cam pin 165, is biased in the radially inward direction. A stopper is provided to the concavities 161a,161b (not shown in the figures), for controlling the limits of the rotational movement of the cam pin 165 by contacting the outer peripheral surface of the cam pin 165. Further, the large diameter lumens 13,14 (not shown in the figures) are shaped such that the outer wall is cut out from the position opposite the concavities 161a, 161b (not shown in the figures) to the distal end side.

In addition, although it is not shown in FIG. 36, a concave portion having the same shape as that of the concave portion 161a is formed in the attachment 161 on the side of the large diameter lumen 14.

Figure 37:
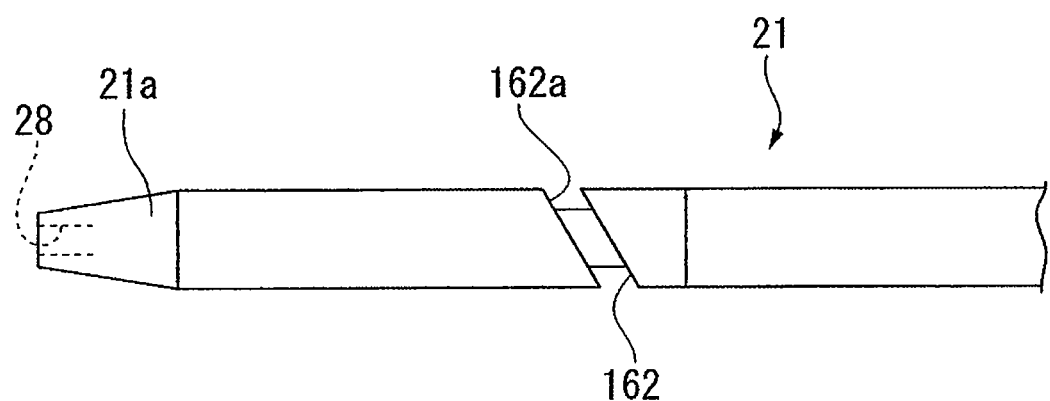
FIG. 37 is a view showing the arm distal end of the medical treatment endoscope.
Figure 38:
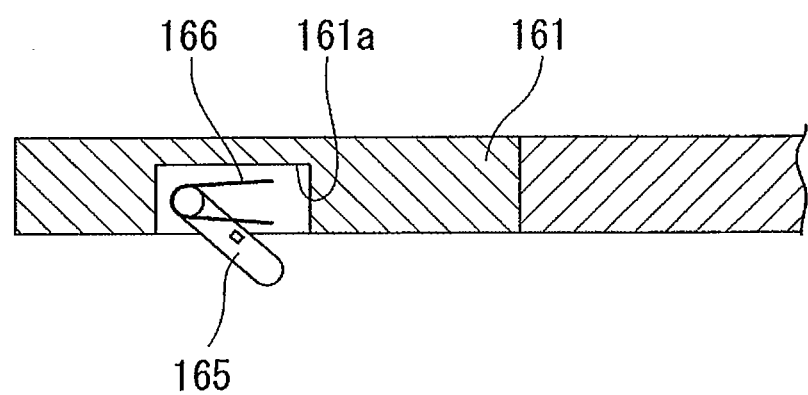
FIG. 38 is a view in partial cross-section showing a modification of the distal end of the medical treatment endoscope.

As shown in FIG. 37, an inclined groove 162 is formed to the arm distal end part 21 which is inclined so as to form an angle with respect to the axis of the arm. The depth of the inclined groove 162 is such that it does not reach the instrument lumen 28. The width of the inclined groove 162 is a width capable of engagement with the cam pin 165.

In this medical treatment endoscope 160, the operator first inserts the arm 20 from the middle openings 17,18 of the medical treatment endoscope into the large diameter lumens 13,14. Next, the tapered end 21a of the arm 20 is projected out from the distal end of the large lumens 13,14. When the arm 20 moves toward the distal end side with respect to the large diameter lumens 13,14 at the arm distal end part 21, and the position of the inclined groove 162 reaches the position of the cam pin 165, the cam pin 165 is projected in the radially inward direction of the attachment 161 by the torsion spring 166. Next, the operator pulls the arm 20 toward the proximal end side with respect to the large diameter lumens 13,14. As a result, the cam pin 165 and the wall surface on the distal end side of the inclined groove 162 contact. The wall surface of the inclined groove 162 swings with respect to the cam pin 165 in accordance with the pulling of the arm 29 toward the proximal end side. As a result, a positional relationship results in which the arm distal end part 21 engages with the cam pin 165 and the arm distal end part 21 moves toward the proximal end side while rotating about the axis of the arm 20, so that the cam pin 165 reaches the distal end side end 162a of the inclined groove 162. By pulling the arm 20 toward the proximal end side, the operator also generates a pulling force on the inclined groove 162 toward the proximal end side. However, since the arm 20 is supported by the cam pin 165 at the distal end side end 162a, it does not move farther toward the proximal end side. For this reason, the position of rotation about the circumference of the arm distal end part 21 is determined to be the specific rotational position at which the cam pin 165 is located at the distal end side end 162a of the inclined grooves 162.

When withdrawing the arm 20 from the large diameter lumens 13,14 once the procedure is completed, the contact between the cam pin 165 and the inclined groove 162 is released by moving the arm 20 to the distal end side of the large diameter lumens. The wire 164, one end of which is connected to the middle are of the cam pin 165 and the other end of which extends toward the proximal end side via the inside of the wall of the large diameter lumens 13,14 or the medical treatment endoscope 160, is then pulled toward the proximal end side of the arm 20. As a result, the cam pin 165 is pulled by the wire 164, and one end undergoes rotational movement in the radially outward direction about the rotational center. With the cam pin 165 housed inside the concavity 161a in the lateral wall of the attachment 161, the arm 20 is withdrawn from the large diameter lumens 13,14 by pulling the arm 20 toward the proximal end side of the large diameter lumens 13,14 while pulling the wire 164 toward the proximal end side of the arm 20.

In this medical treatment endoscope, the inclined groove 162 functions as an inclined cam surface for guiding the cam pin 165. The cam pin 165 is guided by the inclined groove 162, and is positioned on the distal end side end 162a. As a result, the rotational position of the arm 20 about the axis can be positioned and fixed in place with respect to the medical treatment endoscope 160. Further, in this embodiment, a cam pin 165 and a torsion spring 166 are present, and a freely attaching and releasing attachment 161 is provided to the distal end of the medical treatment endoscope. As a result, it is possible to set the rotational position of the arm for a medical treatment endoscope which does not have a structure for holding the rotational position of the arm. Further, since this attachment 161 can be released from the medical treatment endoscope 160 and discarded after use, it is possible to reduce the time and cost associated with cleaning very small parts such as the concavity 161a, cam pin 165, etc.

Next, a fifteenth embodiment of the present invention will be explained with reference to FIGS. 39 and 40. The medical treatment endoscope 170 according to this embodiment differs from the preceding medical treatment endoscopes with respect to the internal design of the large diameter lumen and the design of the arm distal end.

Figure 39:
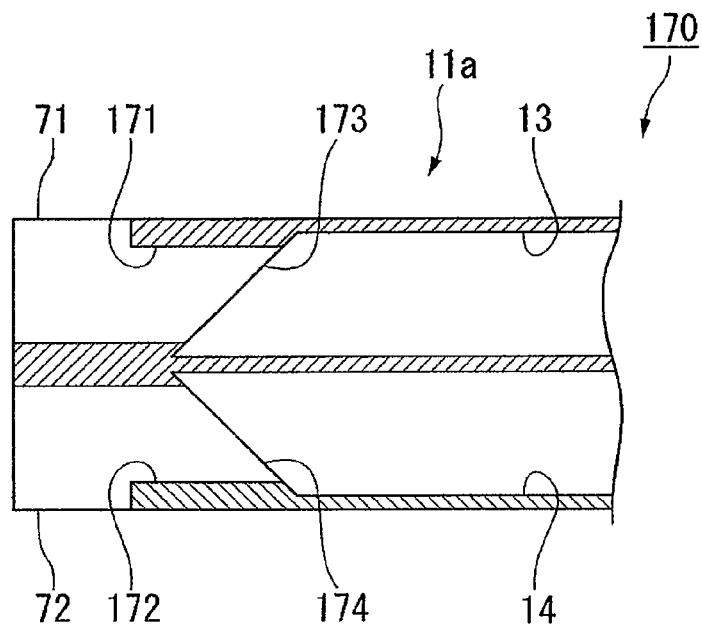
FIG. 39 is a view in partial cross-section showing the distal end of the medical treatment endoscope according to a fifteenth embodiment of the present invention.

As shown in FIG. 39, the large diameter lumens 13,14 have diameters that are relatively larger than the outer diameter of the cylindrical part of the arm. In addition, reduced diameter parts 171,172 is provided to the distal end of the large diameter lumens 13,14, these reduced diameter parts 171,172 having a diameter which is reduced to a value which permits the insertion of the arm 20 in a freely advancing and retracting manner. First inclined end surfaces 173,174, which are inclined in the axial direction, are formed to the proximal end lateral end surface of the reduced diameter parts.

Figure 40:
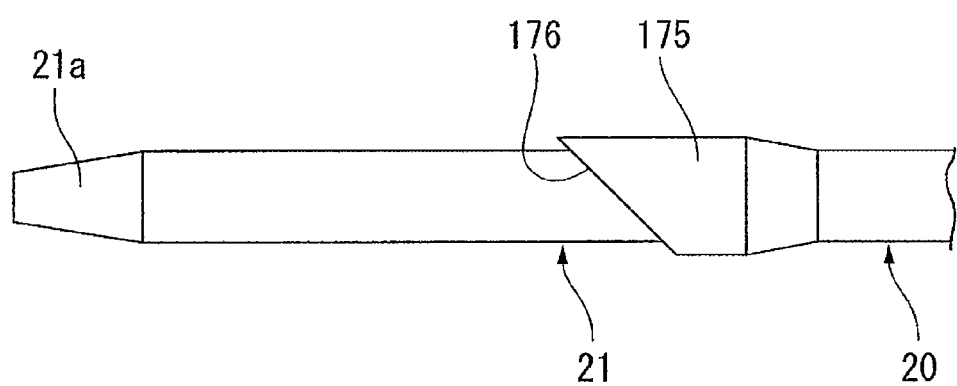
FIG. 40 is a view showing the arm distal end of the medical treatment endoscope.

As shown in FIG. 40, a cylinder body 175 which expands in the radially outward from the arm 20 is provided to the arm distal end part 21. A second inclined end surface 176 having an inclined angle corresponding to the first inclined end surface 173,174 is formed to the cylindrical body 175.

In this medical treatment endoscope, the operator first inserts the arm 20 from the middle openings 17,18 of the medical treatment endoscope 170 into the large diameter lumens 13,14. Next, the arm 20 is moved toward the distal end side with respect to the large diameter lumens 13,14 at the arm distal end part 21, bringing the first inclined end surfaces 173,174 into contact with the second inclined end surface 176. The first inclined end surfaces 173,174 and the second inclined end surface 176 undergo relative rotational movement about the axis so that the area where they respectively contact one another slides. At the position where the respective surfaces of the first incline end surfaces 173, 174 and the second inclined end surface 176 contact, the position of the arm distal end part 21 and the large diameter lumens 13,14 along the circumference is then positioned to a specific rotational position.

When withdrawing the arm 20 from the large diameter lumens 13,14 once the procedure is completed, the arm 20 is pulled toward the proximal end side with respect to the large diameter lumens 13,14, and the arm 20 is withdrawn from the large diameter lumens 13,14.

In this embodiment, the first inclined end surfaces 173,174 formed to the large diameter lumens 13,14, and the second inclined end surface 176 formed to the arm 20 each function as inclined cam surfaces. By moving the arm 20 toward the distal end with respect to the large diameter lumens 13,14, the first inclined end surfaces 173,174 and the second inclined end surface 176 slide and undergo relative rotational movement about the axis. As a result, it is possible to position and fix in place the rotational position of the arm 20 about the axis with respect to the medical treatment endoscope 170. In other words, positioning about the circumference can be carried out by merely pushing the arm 20 into the distal end side of the medical treatment endoscope 170. Thus, the positioning operation can be simplified.

Further, when withdrawing the arm 20 from the large diameters lumens 13,14, it is sufficient to merely pull the arm 20 toward the proximal end side of the medical treatment endoscope 170. Thus, the operation to withdraw the arm 20 is simple.

Next, a sixteenth embodiment of the present invention will be explained with reference to FIGS. 41 and 42. The medical treatment endoscope according to this embodiment differs from the preceding medical treatment endoscope 1 with respect to the internal design of the large diameter lumen and the design of the arm distal end.

Figure 41:
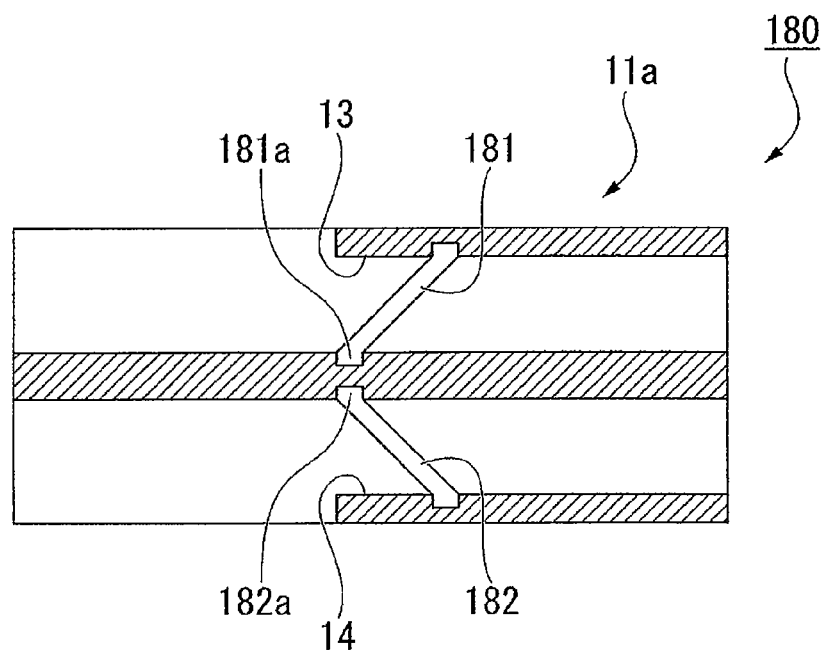
FIG. 41 is a cross-sectional view showing the distal end of the medical treatment endoscope according to a sixteenth embodiment of the present invention.

As shown in FIG. 41, inclined grooves 181,182 are formed to the inner peripheral surface of the large diameter lumens 13,14 at the distal end thereof. These inclined grooves 181, 182 form an angle with respect to the respective center axes of the large diameter lumens 13,14.

Figure 42:
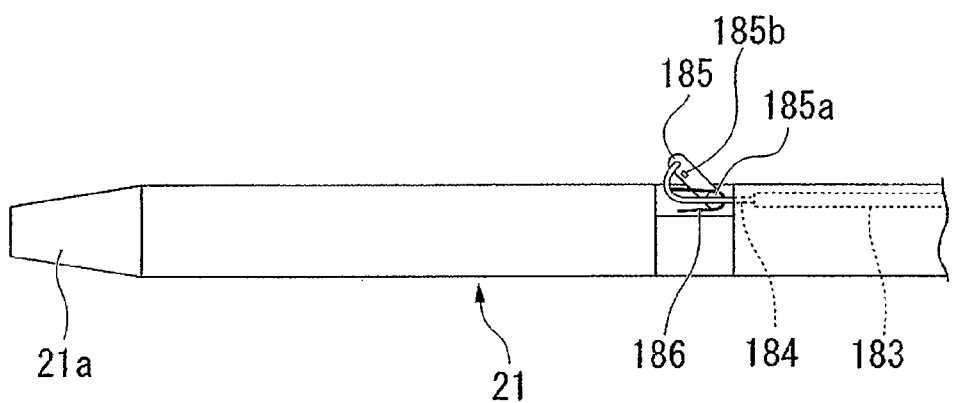
FIG. 42 is a view showing the arm distal end of the medical treatment endoscope.

As shown in FIG. 42, a cam pin 185 is provided to the arm distal end part 21. One end 185a of cam pin 185 is supported by the outer peripheral surface of the arm distal end part 21, with cam pin 185 undergoing rotational movement in the radially outward direction centered about this end 185a. A torsion spring 186 is wound around the end 185a of the cam pin 185. One end of the torsion spring 186 contacts the outer peripheral surface of the arm distal end part 21 and the other end of the torsion spring 186 biases a projection 185b formed to the middle part of the cam pin 185 in the radially outward direction. One end of a wire 184 is connected to the cam pin 185, with the wire 184 inserted into a coil sheath 183 provided inside the lateral wall of the arm 20 and extending toward the proximal end side. The wire 184 projects out from the proximal end side of the arm 20 and is guided to the arm operating portion 30.

In a medical treatment endoscope of this design, the operator inserts the arm 20 from the middle openings 17,18 into the large diameter lumens 13,14. Next, when the position of the cam pin 185 along the axes of the large diameter lumens 13,14 at the arm distal end part 21 is positioned at the inclined grooves 181,182 of the large diameter lumens 13,14, the cam pin 185 projects in the radially outward direction of the arm distal end part 21 due to the torsion spring 186. When the operator moves the arm 20 farther distally with respect to the large diameter lumens 13,14, the other end of the cam pin 185 is pressed against and slides along the wall surface of the inclined grooves 181,182, moving toward the distal end side of the large diameter lumens 13,14 while undergoing rotation about the center axes of the large diameter lumens 13,14. The arm 20 also rotates about the axis at this time. When the arm is moved so that the cam pin 185 is positioned at the distal end lateral end parts 181a,182a of the lateral grooves 181,182, the cam pin 185 is not able to moved farther toward the distal end side. As a result, the position of rotation about the circumference of the arm distal end part 21 is determined to be the specific rotational position at which the cam pin 185 is located at the distal end lateral end parts 181a,182a of the inclined grooves 181,182. Further, the arm 20 is pulled toward the proximal end side when withdrawing the arm 20 from the large diameter lumens 13,14 once the procedure is completed. As a result, the cam pin 185 undergoes rotational movement in the radially outward direction from the arm distal end part 21 due to the force received from the proximal end lateral end surface of the incline grooves 181,182, employing the one end 185a as the center of rotation. The cam pin 185 is thereby housed inside the lateral wall of the arm distal end part 21. In this state, the arm 20 can be withdrawn from the large diameter lumens 13,14 by means of the operator pulling the arm toward the proximal end side of the large diameter lumens 13,14, while pulling the wire 184 toward the proximal side of the arm 20.

In this embodiment, the inclined grooves 181,182 function as an inclined cam surface for guiding the cam pin 185. The cam pin 185 is guided by the inclined grooves 181,182, and is positioned on the distal end lateral end parts 181a,182a. As a result, the rotational position of the arm distal end part 21 about the axis can be positioned and fixed in place with respect to the medical treatment endoscope 180.

Next, a seventeenth embodiment of the present invention will be described with reference to FIGS. 43A and 43B. A medical treatment endoscope 190 according to this embodiment is different from the medical treatment endoscope 1 in that the internal configuration of the large diameter lumen and the configuration of the arm distal end portion are different.

Figure 43A:
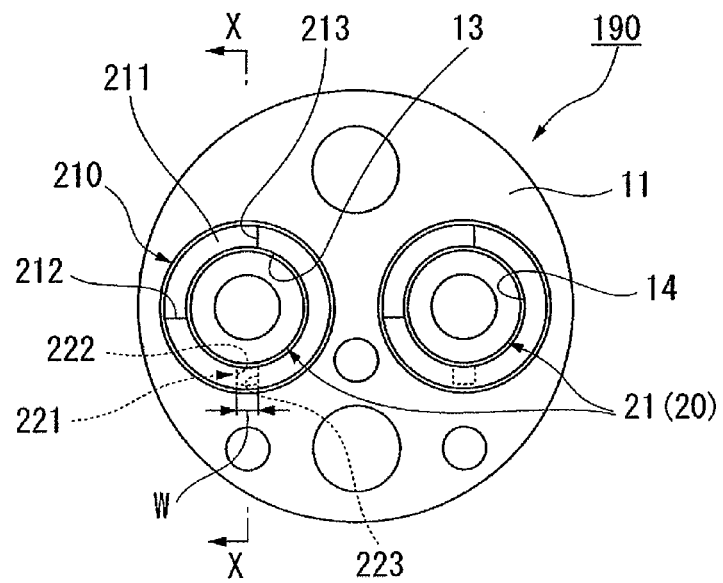
FIG. 43A is a front view showing the medical treatment endoscope according to a seventeenth embodiment of the present invention.
Figure 43B:
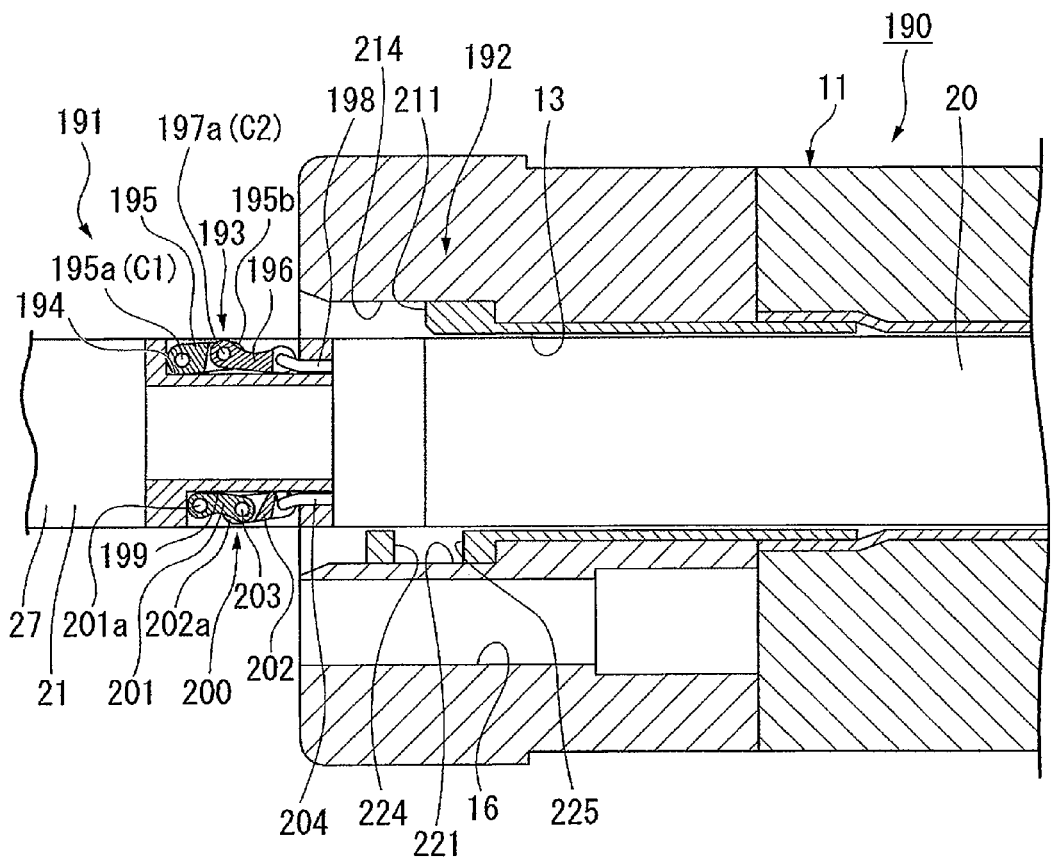
FIG. 43B is a partial sectional view showing a distal end of the medical treatment endoscope.
Figure 44:
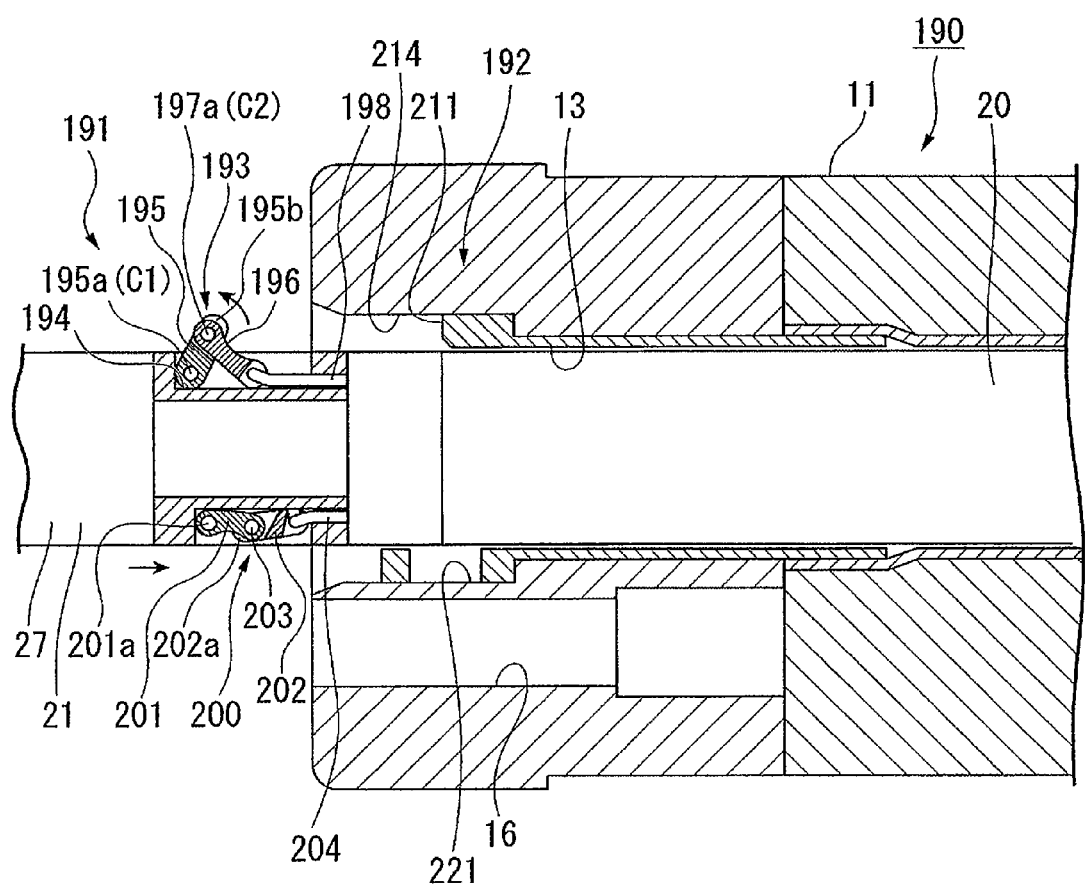
FIG. 44 is a diagram showing an operation of the medical treatment endoscope in use.

As shown in FIGS. 43A and 43B, the medical treatment endoscope 190 includes an engagement mechanism 191 which is formed in the arm distal end portion 21 and an engaged member 192 which is formed inside the distal end of the large diameter lumens 13.

The engagement mechanism 191 includes a first stopper 193 which is formed inside a concave portion 194 formed on the outer surface of the arm distal end portion 21 on the proximal end side of the second bending part 27 and a second stopper 200 which is formed inside a concave portion 199 formed in the outer surface at a position facing the first stopper 193 with the axis of the arm distal end portion 21 interposed therebetween.

The first stopper 193 includes an engaging member 195 of which the other end 195b turns about one end 195a serving as the turning center in a direction moving away from the arm distal end portion 21, a link member 196 which is rotatably connected to the engaging member 195 through a rotation shaft member 197a, and a operating wire 198 which is connected to the proximal end of the link member 196 and extends to the proximal end through the inside of the arm 20.

When the engaging member 195 comes into contact with the bottom portion of the concave portion 194 and is accommodated inside the concave portion 194, a line connecting the turning center C1 of one end 195a of the engaging member 195 and the rotating center C2 of the rotation shaft member is inclined with respect to the axial direction of the arm 20 so as to face outward in the radial direction of the arm 20 in a direction toward the proximal end of the arm 20. For this reason, a pressing force of the operating wire 198 for pressing the engaging member 195 toward the distal end of the arm 20 through the link member 196 is changed to a force for pressing the other end 195b of the engaging member 195 outward in the radial direction of the arm 20.

The second stopper 200 has the same configuration as that of the first stopper 193, and includes a link member 201 which turns about one end 201a serving as the turning center, an engaging member 202 which is rotatably connected to the link member 201 through a rotation shaft member 203, and a operating wire 204 which is connected to the proximal end of the engaging member 202 so as to extend to the proximal end in the inside of the arm 20.

The engaged member 192 includes a contact wall portion 211 which engages with the engaging member 195 of the first stopper 193 and a concave portion 221 which engages with the engaging member 202 of the second stopper 200.

As shown in FIG. 43A, the contact wall portion 211 is formed in a shape in which the large diameter lumen 13 is cut in the range of substantially 90° in the circumferential direction of the large diameter lumen 13 between a first wall 212 and a second wall 213 when viewed from the distal end of the large diameter lumen 13.

The concave portion 221 is formed on the opposite side of the contact wall portion 211 in the radial direction of the large diameter lumen 13. The concave portion 221 includes wall portions 222 and 223 which are opened inward in the radial direction of the large diameter lumen 13 and extend in the axial direction of the large diameter lumen 13, and wall portions 224 and 225 (see FIG. 43B) which extend in the radial direction of the large diameter lumen 13. In addition, it is desirable to set the width W when the concave portion 221 is viewed from the distal end side thereof to the size in which at least a part in the vicinity of the rotation shaft member 203 connecting the link member 201 to the engaging member 202 can be inserted and the connection portion between the link member 201 and the engaging member 202 can simultaneously come into contact with the wall portions 222 and 223.

An operation in the use of the medical treatment endoscope 190 having the above-described configuration according to this embodiment will be described.

Before using the medical treatment endoscope 190, operating wires 198 and 204 are pulled toward the proximal end of the arm 20 so that the engaged members 195 and 202 are respectively accommodated inside the concave portions 194 and 199.

Next, the operator inserts the arm 20 to each of the large diameter lumens 13 and 14 of the insertion portion 11, and pushes out the arm distal end portion 21 from the distal end of the insertion portion 11 as shown in FIG. 43B.

Thereafter, the operator presses the operating wire 198 to the distal end. Then, the engaging member 195 is pressed toward the distal end through the link member 196 connected to the operating wire 198, and the other end 195b of the engaging member 195 turns outward in the radial direction about one end 195a serving as the turning center so as to protrude outward in the radial direction of the arm 20.

The operator aligns the position of the proximal end of the arm 20 to a predetermined position of the stopper 19. Then, the arm 20 rotates in the inside of each of the large diameter lumens 13,14 so as to be aligned to a predetermined direction in accordance with the operation in which the operator aligns the direction of the arm 20.

Figure 45A:
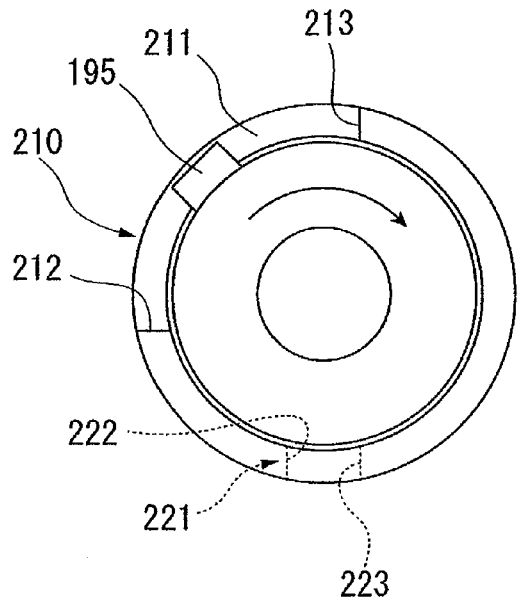
FIGS. 45A and 45B are diagrams showing an operation of the medical treatment endoscope in use.
Figure 45B:
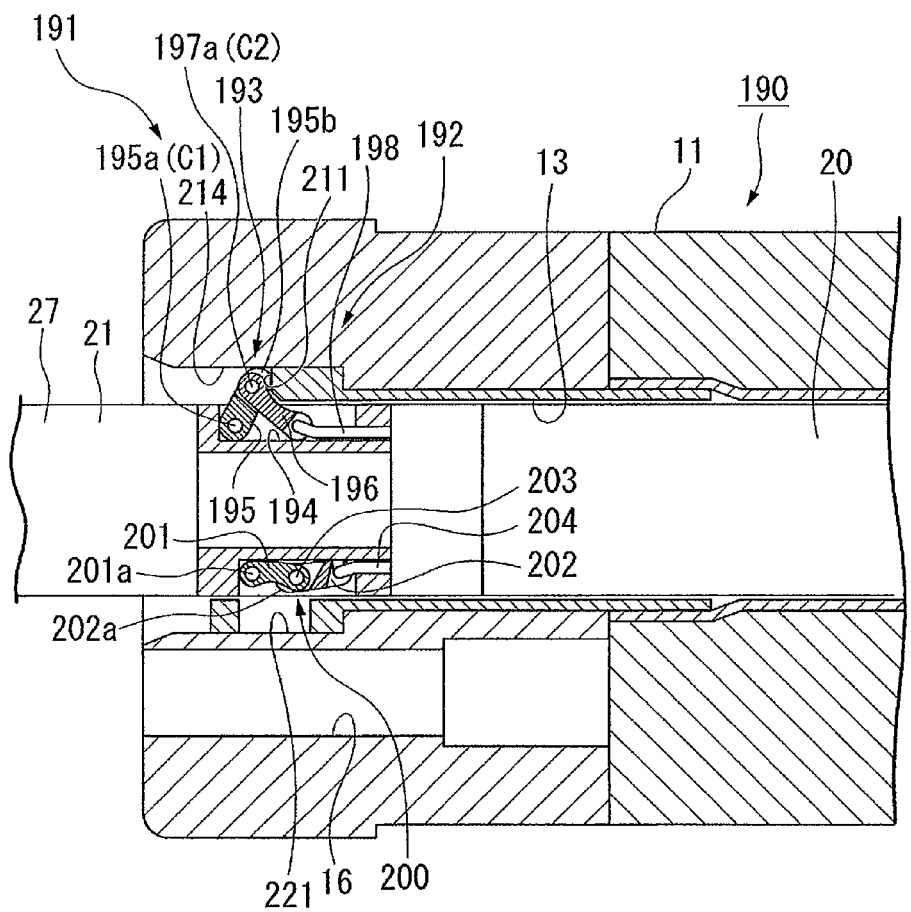
Figure 46A:
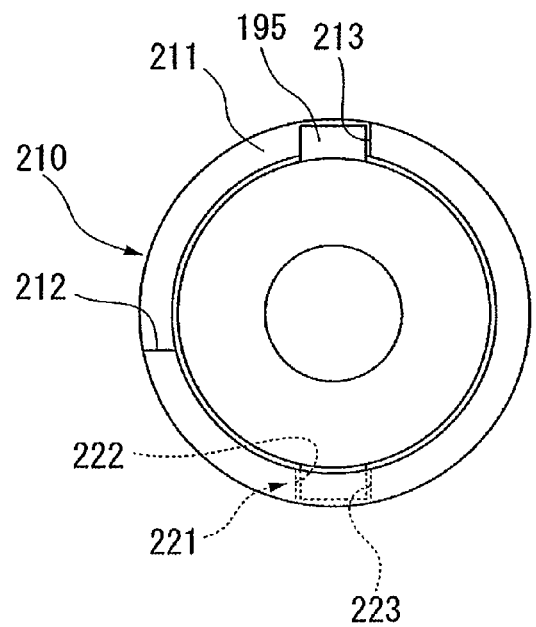
FIGS. 46A and 46B are diagrams showing an operation of medical the treatment endoscope in use.
Figure 46B:
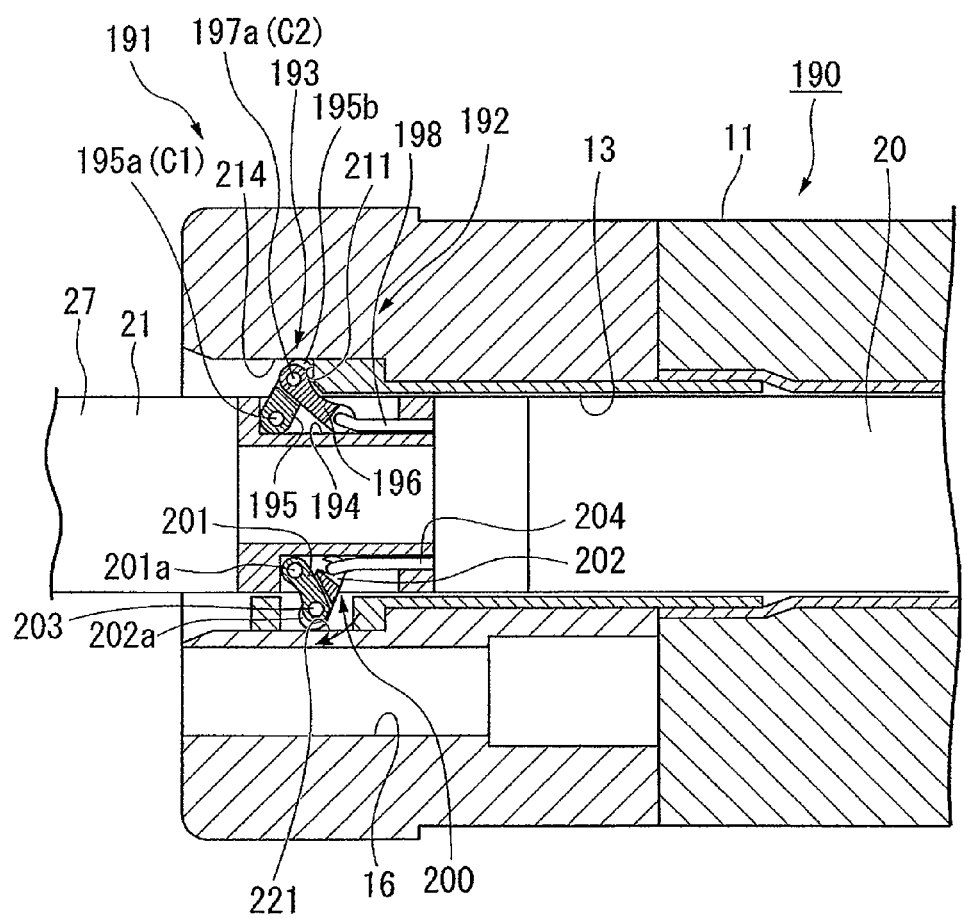

In the state where the engaging member 195 is protruded, the operator pulls the arm 20 toward the proximal end of the insertion portion 11. Then, as shown in FIG. 45B, the arm distal end portion 21 moves to the proximal end of the large diameter lumen 13 (or the large diameter lumen 14) of the insertion portion 11, and the engaging member 195 protruding outward in the radial direction of the arm 20 collides with the contact wall portion 211. Subsequently, the operator rotates the arm 20 about the axis of the large diameter lumen 13 so that the second wall 213 comes into contact with the engaging member 195 as shown in FIG. 46A.

In addition, when the proximal end of the arm 20 is press-fitted to a predetermined position of the stopper 19, the engaging member 195 may be located between the first wall 212 and the second wall 213. In this case, the arm 20 may be rotated about the axis of the large diameter lumen 13 (or the large diameter lumen 14) so that the second wall 213 comes into contact with the engaging member 195, and the arm 20 may be pulled toward the proximal end so that the engaging member 195 comes into contact with the contact wall portion 211.

In this state, the operator presses the operating wire 204 toward the distal end of the arm 20. Then, the operating wire 204 presses the link member 201 through the engaging member 202, and the link member 201 turns about one end 201a serving as the turning center. Then, the engaging member 202 enters and engages with the inside of the concave portion 221.

Likewise, in the positional relationship in which the first stopper 193 and the second stopper 200 protrude outward in the radial direction of the arm 20 in the inside of the large diameter lumen 13, for example, in the case where an external force is generated so as to move the arm 20 to the distal end of the medical treatment endoscope 190, the engaging member 202 inserted into the concave portion 221 is supported to the wall potion 224 of the concave portion 221 so as to suppress the arm 20 from moving to the distal end of the medical treatment endoscope 190.

In addition, in the case where an external force is generated so as to move the arm 20 to the proximal end of the medical treatment endoscope 190, the engaging member 195 is pressed by the contact wall portion 211 and a ceiling surface 214 adjacent to the outside in the radial direction of the contact wall portion 211. At this time, since the other end 195b of the engaging member 195 turns further outward in the radial direction about one end 195a serving as the turning center, the arm 20 is pressed and fixed to the inner wall surface of the large diameter lumen 13 by means of the turning operation of the engaging member 195.

Further, in the case where an external force is generated in the medical treatment endoscope 190 so as to rotate arm 20 about the axis of the large diameter lumen 13, the arm 20 is suppressed from rotating about the axis of the large diameter lumen 13 by means of the link member 201 and the engaging member 202 supported to the wall portions 222 and 223 formed in the concave portion 221.

According to the medical treatment endoscope 190 of this embodiment, by means of the rotating operation of the arm 20 and the reciprocating operation of the operating wires 198 and 204, it is possible to easily and reliably position the arm 20 in the axial direction and about the circumferential direction of the large diameter lumen. Accordingly, even when a large external force is generated in the medical treatment endoscope 190 so as to move the arm 20 in the rotating direction or a direction toward the distal end or the proximal end, it is possible to reliably fix the arm 20 to the medical treatment endoscope 190.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

For example, in the fourteenth embodiment of the present invention, a design was employed in which the cam pin 165 was supported by an attachment at the proximal end side of the concavity 161a. However, the present invention is not limited thereto. Rather, the same effects as the present invention may be obtained with a design in which the cam pin 165 is supported at the distal end side of the concavity 161a. In this case, positioning of the arm distal end part 21 and the cam pin 165 about the circumference is performed by inserting the arm 20 into the large diameter lumens 13,14 and moving the arm 20 toward the distal end side, to bring the cam pin 165 into contact with the proximal end lateral end part 162b of the inclined groove 162 (see FIG. 37).

In addition, the present invention is not limited to the foregoing description, but is limited to the scope of the appended claims.

What is claimed is:

1. A medical treatment endoscope comprising:
   an endoscope main body which includes an elongated insertion portion having an arm-inserted lumen and an image capturing mechanism disposed in a distal end of the insertion portion;
   an arm bending part which is provided so as to protrude or retract freely from the arm-inserted lumen, has a treatment tool lumen for allowing an endoscope treatment tool to be inserted therethrough and is capable of bending freely; and
   a positioning mechanism which positions the arm bending part in the state of protruding from the arm-inserted lumen with respect to the endoscope main body; and
   an operating portion which operates so as to bend the arm bending part,
   wherein the positioning mechanism includes an engaging member which is provided at a proximal end of the arm bending part, and an engaged member which is provided at an inner wall of a distal end of the arm-inserted lumen and engages with the engaging member at a position where the arm bending part protrudes from an opening of the arm-inserted lumen in at least one of a circumference direction and an axial direction,
wherein the member includes:
a first stopper which freely protrudes from an retracts into an outer peripheral surface of an arm and is connected to the arm, and
a second stopper which freely protrudes or retracts from the outer peripheral surface of the arm and is connected to the arm at a position that faces the first stopper in a radial direction of the arm,
wherein the engaged member includes:
a first wall formed on an inner wall of the arm-inserted lumen outward in the radial direction;
a second wall formed on the inner wall of the arm-inserted lumen outward in the radial direction at a position away from the first wall in the circumferential direction;
a contact wall portion formed in the inner wall of the arm-inserted lumen outward in the radial direction and extending in the circumferential direction at a position between the first wall and the second wall; and
a concave portion formed at a position that faces the second wall,
wherein the second stopper engages with an inside of the concave portion when the second stopper is protruded from the outer peripheral surface of the arm in the state where the first stopper that protrudes from the outer peripheral surface of the arm contacts with the contact wall portion and the second wall.

2. The medical treatment endoscope according to claim 1, wherein the arm bending part comprises
a first bending part which is capable of being bent in four directions and
a second bending part which is formed at a position closer to a proximal end thereof than the first bending part and is capable of being bent in two directions and to be maintained in the bending state.

3. The medical treatment endoscope according to claim 1, wherein the engaging member is capable of protruding from an outer peripheral surface of the arm and to be accommodated inside the outer peripheral surface.

4. The medical treatment endoscope according to claim 1, wherein a holder is formed to the endoscope main body, the holder holds the positioned arm in the endoscope main body in a state in which the position of the arm is determined.

5. The medical treatment endoscope according to claim 1, wherein the positioning mechanism is the arm-inserted lumen, and the arm-inserted lumen bends in a radial direction from a proximal end side to a distal end side of the endoscope main body.

6. The medical treatment endoscope according to claim 1, wherein the positioning mechanism is a plurality of arm-inserted lumens, and a pair of arms are inserted in each of the plurality of arm-inserted lumens which extend away from each other.

* * * * *